US008809499B2

(12) United States Patent
Fan et al.

(10) Patent No.: US 8,809,499 B2
(45) Date of Patent: Aug. 19, 2014

(54) FUSION PROTEIN OF HUMAN FIBROBLAST GROWTH FACTOR-21 AND EXENDIN-4

(75) Inventors: Kai Fan, Chongqing (CN); Zhiquan Zhao, Chongqing (CN); Chun Zhang, Chongqing (CN); Yong Chen, Chongqing (CN); Hua Luo, Chongqing (CN); Li Yang, Chongqing (CN); Honghong Liu, Chongqing (CN)

(73) Assignee: Chongqing Fagen Biomedical Inc., Chongqing (CN)

( * ) Notice: Subject to any disclaimer, the term of this patent is extended or adjusted under 35 U.S.C. 154(b) by 2 days.

(21) Appl. No.: 13/391,226

(22) PCT Filed: Mar. 12, 2010

(86) PCT No.: PCT/CN2010/071026
§ 371 (c)(1),
(2), (4) Date: Feb. 17, 2012

(87) PCT Pub. No.: WO2011/020319
PCT Pub. Date: Feb. 24, 2011

(65) Prior Publication Data
US 2012/0238496 A1    Sep. 20, 2012

(30) Foreign Application Priority Data
Aug. 20, 2009    (CN) .......................... 2009 1 0104653

(51) Int. Cl.
*C07K 14/50* (2006.01)
*C12N 1/21* (2006.01)
*C12N 15/12* (2006.01)
*C12N 15/63* (2006.01)
*C07K 14/605* (2006.01)
*C07K 14/43* (2006.01)
*A61K 38/00* (2006.01)

(52) U.S. Cl.
CPC ............... *C07K 14/43* (2013.01); *C07K 14/605* (2013.01); *C07K 14/50* (2013.01); *A61K 38/00* (2013.01); *C07K 2319/00* (2013.01)
USPC ....... 530/350; 435/69.7; 435/320.1; 435/358; 435/360; 435/255.1; 435/252.8

(58) Field of Classification Search
None
See application file for complete search history.

(56) References Cited

U.S. PATENT DOCUMENTS

| | | | |
|---|---|---|---|
| 7,271,149 | B2 | 9/2007 | Glaesner et al. |
| 2006/0194735 | A1 | 8/2006 | Rosen et al. |
| 2007/0036806 | A1 | 2/2007 | Glaesner et al. |
| 2007/0161087 | A1 | 7/2007 | Glaesner et al. |
| 2008/0025045 | A1 | 1/2008 | Mii |
| 2008/0255045 | A1 | 10/2008 | Cujec et al. |
| 2009/0305986 | A1* | 12/2009 | Belouski et al. .............. 514/12 |
| 2011/0034373 | A1* | 2/2011 | Coskun et al. .............. 514/5.3 |

FOREIGN PATENT DOCUMENTS

| | | | |
|---|---|---|---|
| CA | 2693504 | A1 * | 2/2009 |
| CN | 1483041 | A | 3/2004 |
| CN | 101250547 | A | 8/2008 |
| WO | 2004/020405 | A2 | 3/2004 |
| WO | 2004/110472 | A2 | 12/2004 |
| WO | 2006/028595 | A2 | 3/2006 |
| WO | 2009/020802 | A2 | 2/2009 |

OTHER PUBLICATIONS

International Search Report dated Jun. 24, 2010 as received in application No. PCT/CN2010/071026.
Beenken et al FGF family: biology, pathophysiology and therapy, Nature Reviews Drug Discovery, Mar. 2009, vol. 8, Issue 3, pp. 235-253.
Kharitonenkov A. et al., "FGF-21 as a novel metabolic regulator", Journal of Clinical Investigation, Jun. 1, 2005, vol. 115, Issue 6, pp. 1627-1635.
Eng J. et al., "Isolation and characterization of exendin-4, an exendin-3 analogue, from Heloderma suspectum venom. Further evidence for an exendin receptor on dispersed acini from guinea pig pancreas", The Journal of Biological Chemistry, Apr. 15, 1992, vol. 267, pp. 7402-7405.
Kolterman OG. et al., "Synthetic exendin-4 (Exenatide) significantly reduces postprandial and fasting plasma glucose in subjects with type 2 diabetes", Journal of Clinical Endocrinol Metabolism, Jul. 2003, vol. 88, Issue 7, pp. 3082-3089.
Petersen JS et al., "ZP10—A new GLP-1 agonist that prevents diabetes progression and increases insulin mRNA expression in db/db mice", 38th Annual Meeting of the European Association for the Study of Diabetes (EASD) Budapest, Sep. 1-5, 2002, vol. 45, Suppl. 1, A147, Abstract No. 447, pp. 2.
Vilsbøll T. et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients With Type 2 Diabetes", Diabetes Care, Jun. 2007, vol. 30, No. 6, pp. 1608-1610.
Elbrønd B. et al., "Pharmacokinetics, Pharmacodynamics Safety, and Tolerability of a Single-Dose of NN2211, a Long-Acting Glucagon-Like Peptide 1 Derivative, in Healthy Male Subjects", Emerging Treatments and Technologies, Diabetes Care, Aug. 2002, vol. 25, No. 8, pp. 1398-1404.
Neidigh et al., "Exendin-4 and Glucagon-like-peptide-1: NMR Structural Comparisons in the Solution and Micelle-Associated States", Biochemistry, Oct. 13, 2001, vol. 40, No. 44, pp. 13188-13200.
Rong-jie et al., "Expression, purification and biological assay of recombinant hEGF-hbFGF( 78—154aa) fusion protein", Chinese Journal of Pathophysiology, 2002, vol. 18, No. 4, pp. 367-370.
Nishimura et al., "Identification of a novel FGF, FGF-21, preferentially expressed in the liver", Biochimica et Biophysica Acta(BBA)-Gene Structure and Expression, Jun. 21, 2000, vol. 1492, Issue 1, pp. 203-206.
Micanovic et al., "Different Roles of N- and C-Termini in the Functional Activity of FGF21", Journal of Cellular Physiology, May 2009, vol. 219, Issue 2, pp. 227-234.
Inagaki et al., "Endocrine Regulation of the Fasting Response by PPARα-Mediated Induction of Fibroblast Growth Factor 21", Cell Metabolism, Jun. 2007, vol. 5, pp. 415-425.

(Continued)

Primary Examiner — Christine J Saoud
(74) Attorney, Agent, or Firm — Maschoff Brennan

(57) ABSTRACT

Provided is a fusion protein, which comprises human fibroblast growth factor 21 and glucagon-like-peptide-1 or its analogs. Also provided is the medicament composition comprising the fusion protein, which can be used for treating or preventing obesity, diabetes, hyperglycemia and hyperlipidemia etc.

10 Claims, 7 Drawing Sheets

(56) References Cited

OTHER PUBLICATIONS

Kharitonenkov et al., "Fibroblast Growth Factor-21 as a Therapeutic Agent for Metabolic Diseases", Biodrugs 2008, vol. 22, No. 1, pp. 37-44.

Amer et al., "FGF21 attenuates lipolysis in human adipocytes-A possible link to improved insulin sensitivity", FEBS Letters, May 28, 2008, vol. 582, Issue 12, pp. 1725-1730.

Wente et al., "Fibroblast Growth Factor-21 Improves Pancreatic β-Cell Function and Survival by Activation of Extracellular Signal-Regulated Kinase 1/2 and Akt Signaling Pathways", Diabetes, Sep. 2006, vol. 55, pp. 2470-2478.

Badman et al., "Hepatic Fibroblast Growth Factor 21 Is Regulated by PPARα and Is a Key Mediator of Hepatic Lipid Metabolism in Ketotic States", Cell Metabolism, Jun. 2007, vol. 5, Issue 6, pp. 426-437.

Kharitonenkov et al., "The Metabolic State of Diabetic Monkeys Is Regulated by Fibroblast Growth Factor-21", Endocrinology, Feb. 2007, vol. 148, Issue 2, pp. 774-781.

Nielsen et al., "Pharmacology of exenatide (synthetic exendin-4): a potential therapeutic for improved glycemic control of type 2 diabetes", Regulatory Peptides, Feb. 15, 2004, vol. 117, Issue 2, pp. 77-88.

Vaidya et al., "Glucagon Like Peptides-1 Modulators as Newer Target for Diabetes", Current Drug Targets, Oct. 2008, vol. 9, No. 10, pp. 911-920.

Arulmozhi et al., "GLP-1 based therapy for type 2 diabetes", European Journal of Pharmaceutical Sciences, May 2006, vol. 28, Issue 1-2, pp. 96-108.

Mojsov et al., "Preproglucagon Gene Expression in Pancreas and Intestine Diversifies at the Level of Post-translational Processing", The Journal of Biological Chemistry, Sep. 5, 1986, vol. 261, No. 25, pp. 11880-11889.

Kieffer et al., "The Glucagon-Like Peptides", Endocrine Reviews, Dec. 1, 1999, vol. 20, Issue 6, pp. 876-913.

N. Koyama et al., "A novel procedure for the preparation of biologically active recombinant peptides using a cyanylation reaction" J Biotechnol. Feb. 28, 1994;32(3):273-81.

* cited by examiner

```
                    *         20         *         40
FGF-21 : HPIPDSSPLLQFGGQVRQRYLYTDDAQQTEAHLEIREDGTVG :  42

*         60         *         80
FGF-21 : GAADQSPESLLQLKALKPGVIQILGVKTSRFLCQRPDGALYG :  84

*        100         *        120
FGF-21 : SLHFDPEACSFRELLLEDGYNVYQSEAHGLPLHLPGNKSPHR : 126

*        140         *        160
FGF-21 : DPAPRGPARFLPLPGLPPALPEPPGILAPQPPDVGSSDPLSM : 168

*        180
FGF-21 : VGPSQGRSPSYAS : 181
```

Fig 1

```
Glp-1 (7-37)   1  HAEGTFTSDVSSYLEGQAAKEFIAWLVKG---RG           31
Exendin-4      1  HGEGTFTSDLSKQMEEEAVRLFIEWLKNGGPSSGAPPPS      39
```

Fig 2

|  |  | His | Gly | Glu | Gly | Thr | Phe | Thr | Ser | Asp | Leu | Ser | Lys | Gln | Met | Glu |
|---|---|---|---|---|---|---|---|---|---|---|---|---|---|---|---|---|
|  | 1 | CAC | GGT | GAA | GGT | ACC | TTT | ACC | TCT | GAT | CTG | TCT | AAA | CAG | ATG | GAA |
|  |  | Glu | Glu | Ala | Val | Arg | Leu | Phe | Ile | Glu | Trp | Leu | Lys | Asn | Gly | Gly |
|  | 46 | GAG | GAA | GCC | GTT | CGT | CTG | TTT | ATT | GAA | TGG | CTG | AAA | AAT | GGT | GGT |
|  |  | Pro | Ser | Ser | Gly | Ala | Pro | Pro | Pro | Gly | Gly | Gly | Gly | Ser | His |
|  | 91 | CCA | TCT | TCT | GGT | GCA | CCA | CCT | CCA | GGT | GGC | GGC | GGT | GGT | TCT | CAC |
|  |  | Pro | Ile | Pro | Asp | Ser | Ser | Pro | Leu | Leu | Gln | Phe | Gly | Gly | Gln | Val |
|  | 136 | CCA | ATC | CCA | GAT | TCT | AGT | CCA | CTG | TTA | CAA | TTC | GGA | GGT | CAG | GTT |
|  |  | Arg | Gln | Arg | Tyr | Leu | Tyr | Thr | Asp | Asp | Ala | Gln | Gln | Thr | Glu | Ala |
|  | 181 | CGT | CAA | CGT | TAT | CTG | TAT | ACC | GAT | GAC | GCA | CAG | CAG | ACC | GAA | GCC |
|  |  | His | Leu | Glu | Ile | Arg | Glu | Asp | Gly | Thr | Val | Gly | Gly | Ala | Ala | Asp |
|  | 226 | CAT | TTG | GAA | ATT | CGT | GAA | GAT | GGA | ACC | GTT | GGT | GGT | GCT | GCC | GAT |
|  |  | Gln | Ser | Pro | Glu | Ser | Leu | Leu | Gln | Leu | Lys | Ala | Leu | Lys | Pro | Gly |
|  | 271 | CAA | TCT | CCT | GAA | TCA | CTG | TTA | CAG | CTG | AAA | GCA | TTG | AAA | CCA | GGA |
|  |  | Val | Ile | Gln | Ile | Leu | Gly | Val | Lys | Thr | Ser | Arg | Phe | Leu | Cys | Gln |
|  | 316 | GTT | ATT | CAG | ATT | CTG | GGT | GTC | AAA | ACC | TCT | CGT | TTT | TTA | TGT | CAA |
|  |  | Arg | Pro | Asp | Gly | Ala | Leu | Tyr | Gly | Ser | Leu | His | Phe | Asp | Pro | Glu |
|  | 361 | CGT | CCT | GAC | GGT | GCC | CTG | TAT | GGA | AGT | TTG | CAT | TTT | GAT | CCA | GAA |
|  |  | Ala | Cys | Ser | Phe | Arg | Glu | Leu | Leu | Leu | Glu | Asp | Gly | Tyr | Asn | Val |
|  | 406 | GCC | TGT | TCT | TTT | CGT | GAA | CTG | TTA | CTG | GAA | GAT | GGT | TAT | AAT | GTT |
|  |  | Tyr | Gln | Ser | Glu | Ala | His | Gly | Leu | Pro | Leu | His | Leu | Pro | Gly | Asn |
|  | 451 | TAT | CAG | TCA | GAA | GCC | CAC | GGT | TTG | CCT | CTG | CAT | TTA | CCA | GGA | AAT |
|  |  | Lys | Ser | Pro | His | Arg | Asp | Pro | Ala | Pro | Arg | Gly | Pro | Ala | Arg | Phe |
|  | 496 | AAA | TCT | CCT | CAT | CGT | GAC | CCA | GCA | CCT | CGT | GGT | CCA | GCC | CGT | TTT |
|  |  | Leu | Pro | Leu | Pro | Gly | Leu | Pro | Pro | Ala | Leu | Pro | Glu | Pro | Pro | Gly |
|  | 541 | CTG | CCA | TTG | CCA | GGT | CTG | CCT | CCA | GCT | CTG | CCT | GAA | CCA | CCT | GGT |
|  |  | Ile | Leu | Ala | Pro | Gln | Pro | Pro | Asp | Val | Gly | Ser | Ser | Asp | Pro | Leu |
|  | 586 | ATT | CTG | GCC | CCA | CAG | CCT | CCA | GAT | GTT | GGT | AGT | TCT | GAT | CCT | CTG |
|  |  | Ser | Met | Val | Gly | Pro | Ser | Gln | Gly | Arg | Ser | Pro | Ser | Tyr | Ala | Ser |
|  | 631 | TCA | ATG | GTC | GGT | CCA | TCT | CAA | GGT | CGT | AGT | CCT | TCT | TAT | GCA | TCA |
|  |  | *** | *** | Gly | Ser |  |  |  |  |  |  |  |  |  |  |  |
|  | 676 | TGA | TAA | GGA | TCC |  |  |  |  |  |  |  |  |  |  |  |

Fig 3

```
                            SEQUENCE LISTING

<160> NUMBER OF SEQ ID NOS: 58

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
<212> TYPE: PRT
<213> ORGANISM: Heloderma suspectum

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Pro Ser
         35

<210> SEQ ID NO 4
<211> LENGTH: 543
<212> TYPE: DNA
<213> ORGANISM: Artificial Sequence
<220> FEATURE:
<223> OTHER INFORMATION: Synthetic cDNA for FGF-21

<400> SEQUENCE: 4
cacccaatcc cagattctag tccactgtta caattcggag gtcaggttcg tcaacgttat      60
ctgtataccg atgacgcaca gcagaccgaa gcccatttgg aaattcgtga agatggaacc     120
gttggtggtg ctgccgatca atctcctgaa tcactgttac agctgaaagc attgaaacca     180
ggagttattc agattctggg tgtcaaaacc tctcgttttt atgtcaacg tcctgacggt      240
gccctgtatg aagtttgca ttttgatcca gaagcctgtt cttttcgtga actgttactg      300
gaagatggtt ataatgttta tcagtcagaa gcccacggtt gcctctgca tttaccagga      360
aataaatctc ctcatcgtga cccagcacct cgtggtccag cccgttttct gccattgcca     420
ggtctgcctc cagctctgcc tgaaccacct ggtattctgg cccacagcc tccagatgtt      480
ggtagttctg atcctctgtc aatggtcggt ccatctcaag gtcgtagtcc ttcttatgca     540
tca                                                                    543

<210> SEQ ID NO 5
<211> LENGTH: 117
<212> TYPE: DNA
<213> ORGANISM: Artificial Sequence
<220> FEATURE:
<223> OTHER INFORMATION: Synthetic cDNA for Exendin-4

<400> SEQUENCE: 5
catggtgaag gtacctttac ctctgatctg tctaaacaga tggaagaaga agccgttcgt      60
ctgtttattg aatggctgaa aaatggtggt ccatcttctg gtgccccacc accatct        117

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
gccatatgca tggtgaaggt acc                                              23

<210> SEQ ID NO 7
<211> LENGTH: 39
<212> TYPE: DNA
<213> ORGANISM: Artificial Sequence
<220> FEATURE:
<223> OTHER INFORMATION: Synthetic Primer

<400> SEQUENCE: 7
gagaaccacc gccgccacca gatggaggtg gggcaccag                             39

<210> SEQ ID NO 8
<211> LENGTH: 39
<212> TYPE: DNA
<213> ORGANISM: Artificial Sequence
<220> FEATURE:
<223> OTHER INFORMATION: Synthetic Primer

<400> SEQUENCE: 8
ctggtggcgg cggtggttct cacccaatcc cagattcta                                39

<210> SEQ ID NO 9
<211> LENGTH: 24
<212> TYPE: DNA
<213> ORGANISM: Artificial Sequence
<220> FEATURE:
<223> OTHER INFORMATION: Synthetic Primer

<400> SEQUENCE: 9
gcggatcctt atcatgatgc ataa                                                24

<210> SEQ ID NO 10
<211> LENGTH: 687
<212> TYPE: DNA
<213> ORGANISM: Artificial Sequence
<220> FEATURE:
<223> OTHER INFORMATION: Synthetic cDNA for Exendin4-L-FGF21

<400> SEQUENCE: 10
cacggtgaag gtacctttac ctctgatctg tctaaacaga tggaagagga agccgttcgt         60
ctgtttattg aatggctgaa aaatggtggt ccatcttctg gtgcaccacc tccaggtggc        120
ggcggtggtt ctcacccaat cccagattct agtccactgt acaattcgg aggtcaggtt        180 cgtcaacgtt atctgtatac cgatgacgca cagcagaccg aagcccattt ggaaattcgt       240
gaagatggaa ccgttggtgg tgctgccgat caatcctcctg aatcactgtt acagctgaaa      300
gcattgaaaa caggagttat tcagattctg ggtgtcaaaa cctctcgttt tttatgtcaa       360
cgtcctgacg gtgccctgta tggaagtttg cattttgatc cagaagcctg ttcttttcgt      420
gaactgttac tggaagatgg ttataatgtt tatcagtcag aagcccacgg tttgcctctg      480
catttaccag gaaataaatc tcctcatcgt gacccagcac tcgtggtcc agcccgtttt      540 ctgccattgc caggtctgcc tccagctctg cctgaaccac ctggtattct ggccccacag       600
cctccagatg ttggtagttc tgatcctctg tcaatggtcg gtccatctca aggtcgtagt       660
ccttcttatg catcatgata aggatcc                                           687

<210> SEQ ID NO 11
<211> LENGTH: 41
<212> TYPE: DNA
<213> ORGANISM: Artificial Sequence
<220> FEATURE:
<223> OTHER INFORMATION: Synthetic Primer

<400> SEQUENCE: 11
gccagagcca ccgccaccgc taccgccgcc acctggaggt g                             41

<210> SEQ ID NO 12
<211> LENGTH: 39
<212> TYPE: DNA
<213> ORGANISM: Artificial Sequence
<220> FEATURE:
<223> OTHER INFORMATION: Synthetic Primer

<400> SEQUENCE: 12
agcggtggcg gtggctctgg cggcggtggt tctcaccca                                39

<210> SEQ ID NO 13
<211> LENGTH: 36
<212> TYPE: DNA

<213> ORGANISM: Artificial Sequence
<220> FEATURE:
<223> OTHER INFORMATION: Synthetic Primer

<400> SEQUENCE: 13
agaatctggg attgggtgtg gaggtggtgc accaga         36

<210> SEQ ID NO 14
<211> LENGTH: 39
<212> TYPE: DNA
<213> ORGANISM: Artificial Sequence
<220> FEATURE:
<223> OTHER INFORMATION: Synthetic Primer

<400> SEQUENCE: 14
ctcgagaaaa gacatggtga aggtactttt acctctgat     39

<210> SEQ ID NO 15
<211> LENGTH: 39
<212> TYPE: DNA
<213> ORGANISM: Artificial Sequence
<220> FEATURE:
<223> OTHER INFORMATION: Synthetic Primer

<400> SEQUENCE: 15
ctcgagaaaa gacatggtga aggtactttt acctctgat     39

<210> SEQ ID NO 16
<211> LENGTH: 38
<212> TYPE: DNA
<213> ORGANISM: Artificial Sequence
<220> FEATURE:
<223> OTHER INFORMATION: Synthetic Primer

<400> SEQUENCE: 16
gcggccgctt atcatgatgc ataagaagga ctacgacc      38

<210> SEQ ID NO 17
<211> LENGTH: 5
<212> TYPE: PRT
<213> ORGANISM: Artificial Sequence
<220> FEATURE:
<223> OTHER INFORMATION: Linker (GGGGS)n(S)m n=1, m=0

<400> SEQUENCE: 17

Gly Gly Gly Gly Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Linker (GGGGS)n(S)m n=2, m=0

<400> SEQUENCE: 18

Gly Gly Gly Gly Ser Gly Gly Gly Gly Ser
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Linker (GGGGS)n(S)m n=3, m=0

<400> SEQUENCE: 19

```
Gly Gly Gly Gly Ser Gly Gly Gly Gly Ser Gly Gly Gly Gly Ser
1               5                   10                  15
```

<210> SEQ ID NO 20
<211> LENGTH: 20
<212> TYPE: PRT
<213> ORGANISM: Artificial Sequence
<220> FEATURE:
<223> OTHER INFORMATION: Linker (GGGGS)n(S)m n=4, m=0

<400> SEQUENCE: 20

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 21
<211> LENGTH: 25
<212> TYPE: PRT
<213> ORGANISM: Artificial Sequence
<220> FEATURE:
<223> OTHER INFORMATION: Linker (GGGGS)n(S)m n=5, m=0

<400> SEQUENCE: 21

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 22
<211> LENGTH: 6
<212> TYPE: PRT
<213> ORGANISM: Artificial Sequence
<220> FEATURE:
<223> OTHER INFORMATION: Linker (GGGGS)n(S)m n=1, m=1

<400> SEQUENCE: 22

```
Gly Gly Gly Gly Ser Ser
1               5
```

<210> SEQ ID NO 23
<211> LENGTH: 11
<212> TYPE: PRT
<213> ORGANISM: Artificial Sequence
<220> FEATURE:
<223> OTHER INFORMATION: Linker (GGGGS)n(S)m n=2, m=1

<400> SEQUENCE: 23

```
Gly Gly Gly Gly Ser Gly Gly Gly Gly Ser Ser
1               5                   10
```

<210> SEQ ID NO 24
<211> LENGTH: 16
<212> TYPE: PRT
<213> ORGANISM: Artificial Sequence
<220> FEATURE:
<223> OTHER INFORMATION: Linker (GGGGS)n(S)m n=3, m=1

<400> SEQUENCE: 24

```
Gly Gly Gly Gly Ser Gly Gly Gly Gly Ser Gly Gly Gly Gly Ser Ser
1               5                   10                  15
```

<210> SEQ ID NO 25
<211> LENGTH: 21
<212> TYPE: PRT

```
<213> ORGANISM: Artificial Sequence
<220> FEATURE:
<223> OTHER INFORMATION: Linker (GGGGS)n(S)m n=4, m=1

<400> SEQUENCE: 25

Gly Gly Gly Gly Ser Gly Gly Gly Gly Ser Gly Gly Gly Gly Ser Gly
1               5                   10                  15

Gly Gly Gly Ser Ser
            20

<210> SEQ ID NO 26
<211> LENGTH: 26
<212> TYPE: PRT
<213> ORGANISM: Artificial Sequence
<220> FEATURE:
<223> OTHER INFORMATION: Linker (GGGGS)n(S)m n=5, m=1

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Ser
            20                  25

<210> SEQ ID NO 27
<211> LENGTH: 5
<212> TYPE: PRT
<213> ORGANISM: Artificial Sequence
<220> FEATURE:
<223> OTHER INFORMATION: Linker (GGGGG))n(S)m n=1, m=0

<400> SEQUENCE: 27

Gly Gly Gly Gly Gly
1               5

<210> SEQ ID NO 28
<211> LENGTH: 10
<212> TYPE: PRT
<213> ORGANISM: Artificial Sequence
<220> FEATURE:
<223> OTHER INFORMATION: Linker (GGGGG))n(S)m n=2, m=0

<400> SEQUENCE: 28

Gly Gly Gly Gly Gly Gly Gly Gly Gly Gly
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Linker (GGGGG))n(S)m n=3, m=0

<400> SEQUENCE: 29

Gly Gly Gly Gly Gly Gly Gly Gly Gly Gly Gly Gly Gly Gly Gly
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Linker (GGGGG))n(S)m n=4, m=0

<400> SEQUENCE: 30

Gly Gly Gly Gly Gly Gly Gly Gly Gly Gly Gly Gly Gly Gly Gly Gly
1               5                   10                  15
```

```
Gly Gly Gly Gly
            20

<210> SEQ ID NO 31
<211> LENGTH: 25
<212> TYPE: PRT
<213> ORGANISM: Artificial Sequence
<220> FEATURE:
<223> OTHER INFORMATION: Linker (GGGGG))n(S)m n=5, m=0

<400> SEQUENCE: 31

Gly Gly Gly Gly Gly Gly Gly Gly Gly Gly Gly Gly Gly Gly Gly
1               5                   10                  15

Gly Gly Gly Gly Gly Gly Gly Gly Gly Gly
            20                  25

<210> SEQ ID NO 32
<211> LENGTH: 6
<212> TYPE: PRT
<213> ORGANISM: Artificial Sequence
<220> FEATURE:
<223> OTHER INFORMATION: Linker (GGGGG))n(S)m n=1, m=1

<400> SEQUENCE: 32

Gly Gly Gly Gly Gly Ser
1               5

<210> SEQ ID NO 33
<211> LENGTH: 11
<212> TYPE: PRT
<213> ORGANISM: Artificial Sequence
<220> FEATURE:
<223> OTHER INFORMATION: Linker (GGGGG))n(S)m n=2, m=1

<400> SEQUENCE: 33

Gly Gly Gly Gly Gly Gly Gly Gly Gly Gly Ser
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Linker (GGGGG))n(S)m n=3, m=1

<400> SEQUENCE: 34

Gly Gly Gly Gly Gly Gly Gly Gly Gly Gly Gly Gly Gly Gly Gly Ser
1               5                   10                  15

<210> SEQ ID NO 35
<211> LENGTH: 21
<212> TYPE: PRT
<213> ORGANISM: Artificial Sequence
<220> FEATURE:
<223> OTHER INFORMATION: Linker (GGGGG))n(S)m n=4, m=1

<400> SEQUENCE: 35

Gly Gly Gly Gly Gly Gly Gly Gly Gly Gly Gly Gly Gly Gly Gly Gly
1               5                   10                  15

Gly Gly Gly Gly Ser
            20

<210> SEQ ID NO 36
<211> LENGTH: 26
<212> TYPE: PRT
```

<213> ORGANISM: Artificial Sequence
<220> FEATURE:
<223> OTHER INFORMATION: Linker (GGGGG))n(S)m n=5, m=1

<400> SEQUENCE: 36

Gly Gly Gly Gly Gly Gly Gly Gly Gly Gly Gly Gly Gly Gly Gly
1               5                   10                  15

Gly Gly Gly Gly Gly Gly Gly Gly Gly Ser
            20                  25

<210> SEQ ID NO 37
<211> LENGTH: 7
<212> TYPE: PRT
<213> ORGANISM: Artificial Sequence
<220> FEATURE:
<223> OTHER INFORMATION: Linker (GGGGS)n(SP)m n=1, m=1

<400> SEQUENCE: 37

Gly Gly Gly Gly Ser Ser Pro
1               5

<210> SEQ ID NO 38
<211> LENGTH: 12
<212> TYPE: PRT
<213> ORGANISM: Artificial Sequence
<220> FEATURE:
<223> OTHER INFORMATION: Linker(GGGGS)n(SP)m n=2, m=1

<400> SEQUENCE: 38

Gly Gly Gly Gly Ser Gly Gly Gly Gly Ser Ser Pro
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Linker (GGGGS)n(SP)m n=3, m=1

<400> SEQUENCE: 39

Gly Gly Gly Gly Ser Gly Gly Gly Gly Ser Gly Gly Gly Gly Ser Ser
1               5                   10                  15

Pro

<210> SEQ ID NO 40
<211> LENGTH: 22
<212> TYPE: PRT
<213> ORGANISM: Artificial Sequence
<220> FEATURE:
<223> OTHER INFORMATION: Linker (GGGGS)n(SP)m n=4, m=1

<400> SEQUENCE: 40

Gly Gly Gly Gly Ser Gly Gly Gly Gly Ser Gly Gly Gly Gly Ser Gly
1               5                   10                  15

Gly Gly Gly Ser Ser Pro
            20

<210> SEQ ID NO 41
<211> LENGTH: 27
<212> TYPE: PRT
<213> ORGANISM: Artificial Sequence
<220> FEATURE:
<223> OTHER INFORMATION: Linker (GGGGS)n(SP)m n=5, m=1

<400> SEQUENCE: 41

Gly Gly Gly Gly Ser Gly Gly Gly Ser Gly Gly Gly Ser Gly
1               5                   10                  15

Gly Gly Gly Ser Gly Gly Gly Gly Ser Ser Pro
            20                  25

<210> SEQ ID NO 42
<211> LENGTH: 6
<212> TYPE: PRT
<213> ORGANISM: Artificial Sequence
<220> FEATURE:
<223> OTHER INFORMATION: Linker (PEAPTD)n, n=1

<400> SEQUENCE: 42

Pro Glu Ala Pro Thr Asp
1               5

<210> SEQ ID NO 43
<211> LENGTH: 12
<212> TYPE: PRT
<213> ORGANISM: Artificial Sequence
<220> FEATURE:
<223> OTHER INFORMATION: Linker (PEAPTD)n, n=2

<400> SEQUENCE: 43

Pro Glu Ala Pro Thr Asp Pro Glu Ala Pro Thr Asp
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Linker(PEAPTD)n, n=3

<400> SEQUENCE: 44

Pro Glu Ala Pro Thr Asp Pro Glu Ala Pro Thr Asp Pro Glu Ala Pro
1               5                   10                  15

Thr Asp

<210> SEQ ID NO 45
<211> LENGTH: 24
<212> TYPE: PRT
<213> ORGANISM: Artificial Sequence
<220> FEATURE:
<223> OTHER INFORMATION: Linker (PEAPTD)n, n=4

<400> SEQUENCE: 45

Pro Glu Ala Pro Thr Asp Pro Glu Ala Pro Thr Asp Pro Glu Ala Pro
1               5                   10                  15

Thr Asp Pro Glu Ala Pro Thr Asp
            20

<210> SEQ ID NO 46
<211> LENGTH: 30
<212> TYPE: PRT
<213> ORGANISM: Artificial Sequence
<220> FEATURE:
<223> OTHER INFORMATION: Linker (PEAPTD)n, n=5

<400> SEQUENCE: 46

Pro Glu Ala Pro Thr Asp Pro Glu Ala Pro Thr Asp Pro Glu Ala Pro
1               5                   10                  15

Thr Asp Pro Glu Ala Pro Thr Asp Pro Glu Ala Pro Thr Asp
            20                  25                  30

<210> SEQ ID NO 47
<211> LENGTH: 5
<212> TYPE: PRT
<213> ORGANISM: Artificial Sequence
<220> FEATURE:
<223> OTHER INFORMATION: Linker (SSSSG)n(SP)m, n=1, m=0

<400> SEQUENCE: 47

Ser Ser Ser Ser Gly
1               5

<210> SEQ ID NO 48
<211> LENGTH: 10
<212> TYPE: PRT
<213> ORGANISM: Artificial Sequence
<220> FEATURE:
<223> OTHER INFORMATION: Linker (SSSSG)n(SP)m, n=2, m=0

<400> SEQUENCE: 48

Ser Ser Ser Ser Gly Ser Ser Ser Ser Gly
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Linker (SSSSG)n(SP)m, n=3, m=0

<400> SEQUENCE: 49

Ser Ser Ser Ser Gly Ser Ser Ser Ser Gly Ser Ser Ser Ser Gly
1               5                   10                  15

<210> SEQ ID NO 50
<211> LENGTH: 20
<212> TYPE: PRT
<213> ORGANISM: Artificial Sequence
<220> FEATURE:
<223> OTHER INFORMATION: Linker (SSSSG)n(SP)m, n=4, m=0

<400> SEQUENCE: 50

Ser Ser Ser Ser Gly Ser Ser Ser Ser Gly Ser Ser Ser Ser Gly Ser
1               5                   10                  15

Ser Ser Ser Gly
            20

<210> SEQ ID NO 51
<211> LENGTH: 25
<212> TYPE: PRT
<213> ORGANISM: Artificial Sequence
<220> FEATURE:
<223> OTHER INFORMATION: Linker (SSSSG)n(SP)m, n=5, m=0

<400> SEQUENCE: 51

Ser Ser Ser Ser Gly Ser Ser Ser Ser Gly Ser Ser Ser Ser Gly Ser
1               5                   10                  15

Ser Ser Ser Gly Ser Ser Ser Ser Gly
            20                  25

<210> SEQ ID NO 52
<211> LENGTH: 7
<212> TYPE: PRT
<213> ORGANISM: Artificial Sequence
<220> FEATURE:
<223> OTHER INFORMATION: Linker (SSSSG)n(SP)m, n=1, m=1

```
<400> SEQUENCE: 52

Ser Ser Ser Ser Gly Ser Pro
1               5

<210> SEQ ID NO 53
<211> LENGTH: 12
<212> TYPE: PRT
<213> ORGANISM: Artificial Sequence
<220> FEATURE:
<223> OTHER INFORMATION: Linker (SSSSG)n(SP)m, n=2, m=1

<400> SEQUENCE: 53

Ser Ser Ser Ser Gly Ser Ser Ser Ser Gly Ser Pro
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Linker (SSSSG)n(SP)m, n=3, m=1

<400> SEQUENCE: 54

Ser Ser Ser Ser Gly Ser Ser Ser Ser Gly Ser Ser Ser Ser Gly Ser
1               5                   10                  15

Pro

<210> SEQ ID NO 55
<211> LENGTH: 22
<212> TYPE: PRT
<213> ORGANISM: Artificial Sequence
<220> FEATURE:
<223> OTHER INFORMATION: Linker (SSSSG)n(SP)m, n=4, m=1

<400> SEQUENCE: 55

Ser Ser Ser Ser Gly Ser Ser Ser Ser Gly Ser Ser Ser Ser Gly Ser
1               5                   10                  15

Ser Ser Ser Gly Ser Pro
            20

<210> SEQ ID NO 56
<211> LENGTH: 27
<212> TYPE: PRT
<213> ORGANISM: Artificial Sequence
<220> FEATURE:
<223> OTHER INFORMATION: Linker (SSSSG)n(SP)m, n=5, m=1

<400> SEQUENCE: 56

Ser Ser Ser Ser Gly Ser Ser Ser Ser Gly Ser Ser Ser Ser Gly Ser
1               5                   10                  15

Ser Ser Ser Gly Ser Ser Ser Ser Gly Ser Pro
            20                  25

<210> SEQ ID NO 57
<211> LENGTH: 5
<212> TYPE: PRT
<213> ORGANISM: Artificial Sequence
<220> FEATURE:
<223> OTHER INFORMATION: Linker (SGGGG)

<400> SEQUENCE: 57

Ser Gly Gly Gly Gly
1               5
```

```
<210> SEQ ID NO 58
<211> LENGTH: 227
<212> TYPE: PRT
<213> ORGANISM: Artificial Sequence
<220> FEATURE:
<223> OTHER INFORMATION: Synthetic Exendin4-L-FGF21

<400> SEQUENCE: 58

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Gly Gly Gly Gly Ser His Pro Ile Pro
        35                  40                  45

Asp Ser Ser Pro Leu Leu Gln Phe Gly Gly Gln Val Arg Gln Arg Tyr
50                  55                  60

Leu Tyr Thr Asp Asp Ala Gln Gln Thr Glu Ala His Leu Glu Ile Arg
65                  70                  75                  80

Glu Asp Gly Thr Val Gly Gly Ala Ala Asp Gln Ser Pro Glu Ser Leu
                85                  90                  95

Leu Gln Leu Lys Ala Leu Lys Pro Gly Val Ile Gln Ile Leu Gly Val
            100                 105                 110

Lys Thr Ser Arg Phe Leu Cys Gln Arg Pro Asp Gly Ala Leu Tyr Gly
        115                 120                 125

Ser Leu His Phe Asp Pro Glu Ala Cys Ser Phe Arg Glu Leu Leu Leu
    130                 135                 140

Glu Asp Gly Tyr Asn Val Tyr Gln Ser Glu Ala His Gly Leu Pro Leu
145                 150                 155                 160

His Leu Pro Gly Asn Lys Ser Pro His Arg Asp Pro Ala Pro Arg Gly
                165                 170                 175

Pro Ala Arg Phe Leu Pro Leu Pro Gly Leu Pro Pro Ala Leu Pro Glu
            180                 185                 190

Pro Pro Gly Ile Leu Ala Pro Gln Pro Pro Asp Val Gly Ser Ser Asp
        195                 200                 205

Pro Leu Ser Met Val Gly Pro Ser Gln Gly Arg Ser Pro Ser Tyr Ala
    210                 215                 220

Ser Gly Ser
225
```

FUSION PROTEIN OF HUMAN FIBROBLAST GROWTH FACTOR-21 AND EXENDIN-4

CROSS-REFERENCE TO RELATED APPLICATIONS

This is a U.S. national stage application of international application no. PCT/CN2010/071026, filed Mar. 12, 2010, which claims priority to Chinese patent application no. 200910104653.3, filed Aug. 20, 2009. The foregoing applications are incorporated herein by reference.

TECHNICAL FIELD

The present invention relates to a recombinant protein and use thereof in pharmaceutical application, especially to the fusion protein of human fibroblast growth factor 21 and human glucagon-like-peptide-1, or analogues thereof and use thereof in preparing drugs against obesity, type 2 diabetes and hyperlipidemia; as well as preparation methods thereof.

BACKGROUND

Fibroblast growth factor (FGF) is a series of multi-functional polypeptides, and 18 mammalian fibroblast growth factors (FGF1-FGF10, FGF16-FGF23) have been found. According to the different sequence homology, they are subdivided into 6 subfamilies (Andrew Beenken et al., Nat Rev Drug Discov, 2009, 8(3): 235-253). Fibroblast growth factor 21 (FGF-21) was found for the first time in 2000 by Nishimura et al., (Nishimura T. et al., Biochim Biophys Acta, 2000, 1492: 203-206) from mice embryo. It belongs to the same subfamily as FGF-19 and FGF-23, does not bind heparin, and plays a part in endocrine regulations, such as metabolism of bile acid, cholesterol, glucose and vitamin D, etc.

Human FGF-21 gene is located at chromosome No. 19. The full length of FGF-21 comprises mature FGF-21 protein of 181 amino acids and a signal peptide of 28 amino acids at the N-terminal. Both N- and C-terminal of mature human FGF-21 protein have biological functions: N-terminal amino acids participate in the interaction with FGF receptors; whereas C-terminal amino acids participate in the interaction with beta-Klotho protein (Micanovic R. et al., J Cell Phys, 2009, 219(2): 227-234). Studies on the tissue cell distribution of FGF-21 are mainly at mRNA level, wherein endogenic FGF-21 mRNA was found first in thymus and liver, and then in pancreas, grease as well as in muscular tissues (Inagaki T. et al., Cell Metab, 2007, 5 (6): 415-425). The biological function of human FGF-21 was found while screening novel proteins potentially useful in diabetes treatment by glucose uptake assay (Kharitonenkov A. et al., J Clin Invest, 2005, 115 (6): 1627-1635). Recombinant human FGF-21 protein may stimulate the glucose uptake of differentiated mouse 3T3-L1 cell and human preadipocyte. Being different from the rapid insulin-intermediated utilization of glucose, the glucose uptake effect of FGF-21 can last for a few hours. More importantly, the glucose uptake with FGF-21 is non-insulin dependent, and can be enhanced in the presence of insulin (Alexei Kharitonenkov et al., Biodrugs, 2008, 22 (1): 37-44). Experiments show later that FGF-21 increases the non-insulin dependent glucose uptake by increasing the expression of glucose vectors-1 (GLUT-1) in 3T3-L1 cell and human preadipocyte (Amer P. et al., FEBS Lett, 2008, 582 (12): 1725-1730). Wente W. et al., discovered that (Wente W. et al., Diabetes, 2006, 55: 2470-2478) in isolated mouse pancreas islet cell and INS-1E cell, FGF-21 could increase the transcription, expression and secretion of insulin, thereby preventing programmed cell death intermediated by glycolipid and cell factors, protecting the amount and function of pancreas islet β-cell, as well as inhibiting glucose-mediated release of glucagon. In transgenic mice with high expression of FGF-21 (wherein the concentration of FGF-21 mRNA is 50-150 folds of that of the control), contents of the serum cholesterol, glucose and triglyceride in vivo are decreased significantly, as well as the fasting insulin level; also improved are insulin sensitivity and glucose clearance (Inagaki T, Cell Metab, 2007, 5 (6): 415-425). In contrast, severe metabolism abnormality is found in mice with adenovirus-mediated FGF-21 gene silence, including fatty liver, hypertriglyceridemia, significant increase of free fatty acids and total cholesterol content in serum, as well as decrease of ketones in serum, etc. (Badman M K et al., Cell Metab, 2007, 5 (6): 426-437). In animal models of diabetes of non-human primates, the content of LDL cholesterol could be decreased and HDL cholesterol increased by injecting recombinant human FGF-21, thus reducing risks of suffering from cardiovascular diseases (Kharitonenkov A. et al., Endocrinology, 2007, 148: 774-781). No hypoglycemia, oedema or obesity increase or other side effects is found in animal pharmacodynamic experiments of recombinant human FGF-21 in vivo, demonstrating its promising application prospect and safety.

Owing to its potential value for the treatment of diabetes, relevant drugs of human FGF-21 are now being studied by Lilly and Ambrx Corp. A recombinant human FGF-21 mutant (LP10152) is at phase I clinical trial in Lilly Corp. (Frye C C et al., WO2006/028595), whereas a PEG-modified human FGF-21 protein is on preclinical study in Ambrx and Merck Corp. (Thomas P. et al., US2008/025045).

Biological effects are retained in human FGF-21 with 4 amino acids deleted from the N-terminal (Micanovic R. et al., J Cell Phys, 2009, 219(2): 227-234); also, no decrease of bioactivity is found after local amino acid mutation or (and) deglycosylation (Frye C C et al., WO2006/028595). Therefore, it is now an important part in human FGF-21 research to modify the amino acid sequence.

GLP-1

As a post-translation product of proglucagon gene, glucagon-like-peptide-1 (GLP-1) was found for the first time in 1984 (Majaov S. et al., J Biol Chem, 1986, 261: 11880-11889). The human proglucagon gene is located at chromosome No. 17. It can be expressed not only in pancreatic α-cell, but also in intestinal L-cell, wherein products of genetic transcription and translation are the same and those of post-translation different. In pancreatic α-cell, proglucagon is cleaved into glucagon, enteroglucagon-associated peptides and a major fragment of proglucagon. In intestinal L-cell, proglucagon is cleaved into glucagon-like-peptide-1 (GLP-1), glucagon-like-peptide-2 (GLP-2) and enteroglucagon (Nielsen L L et al., Regul Pept, 2004, 117: 77-88).

The initial GLP-1 produced in intestinal canal is an inactive 37-peptide, wherein a 6-peptide at the N-terminal need to be removed to form GLP-1 (7-37), which has biological activity; and the C-terminal Gly can serve as a substrate of amidase and the peptide is further degraded into GLP-1 (7-36) amide with increased stability in vivo. About 80% of naturally occurring GLP-1 in intestinal canal exists with the latter form (Kieffer T J et al., Endocr Rev, 1999, 25: 876-913). The intestinal L-cell is stimulated to secrete GLP-1 in intestinal canal during food digestion, among which the stimulation of sugar and fat work the strongest. Normally, the concentration of plasma GLP-1 rises significantly at 5-30 minutes after a meal. As an important incretin, GLP-1 mainly possesses with following biological functions, including: (1) binding the specific receptor GLP-1R at pancreas islet β-cell to stimulate the synthesis and release of insulin in correspondance with glucose concentration: the higher the latter, the stronger the former, and vice verse; (2) inhibiting the release of glucagon in pancreas islet α-cell, thus reducing that of glycogen in livers; (3) increasing insulin sensitivity to improve the proliferation and function of pancreas islet β-cell, and to reduce apoptosis; (4) promoting differentiation of precursor pancreas islet cell into mature pancreas islet cell; (5) reducing the rate of stomach evacuation to inhibit appetite (Vaidya, H B et al., Curr Drug Targets, 2008, 9: 911-920).

With many advantages in treating diabetes, however, natural GLP-1 has limited clinical usage because of its short plasma half-life in vivo. A di-peptide is cleaved from the N-terminal of GLP-1 by dipeptidyl peptidase IV (DPP IV), which can specifically recognize Ala2 at the N-terminal; thus degrading GLP-1 into inactive GLP-1 (9-36) and GLP-1(9-37), and making its half-life to be only about 2 minutes. To prolong the half-life of GLP-1 in vivo for better clinical application, studies are now focused on structural improvement of GLP-1 for mutants specifically resisting to the degradation of DPP IV (Arulmozhi D K et al., Eur J Pharm Sci, 2006, 28: 96-108).

Exenatide, which is developed from GLP-1 by Amylin and Lilly Corp., USA, is the first drug against diabetes derived from GLP-1 receptor. Exenatide is a synthetic Exendin-4, which is an effective GLP-1R agonist of a short peptide of 39 amino acids found in *Heloderma horridurn* venom (Eng J et al., J Biol Chem, 1992, 267: 7402-7405). As a GLP-1 analogue, Exendin-4 shares 53% homology with GLP-1 and has Gly2 at the N-terminal, resisting to the degradation from DPP IV and prolonging the plasma half-life. Gly22 of GLP-1 breaks the space structure of helix, while Glu16 of Exendin-4 stabilizes the α-helix. Furthermore, the C-terminal of Exendin-4 comprises 9 amino acids that do not exist in GLP-1, making it to be unlikely digested by Endonuclease, and to be allowed to bind to the N-terminal of GLP-1R, hence enhancing the affinity (Kolterman O G, J Clin Endocrinol Metab, 2003, 88: 3082-3089). Owing to its structural advantages, Exendin-4 performs 5530-fold better than GLP-1 in lowering the level of blood sugar. Additionally, ZP10, a GLP-1 analogue derived from Exendin-4 wherein the C-terminal of Exendin-4 is added with 5-lysine (Petersen J S, Diabetologia, 2002, 45: A147), also exhibits prolonged half-life in blood, and therefore is allowed to be administrated once a day.

Liraglutide, an amidated GLP-1 derivative developed by Novo Nordisk Corp. in Denmark (Vilsbøll T, Diabetes Care, 2007, 30: 1608-1610), has Lys34 of GLP-1 substituted with Arg, as well as a $C_{16}$ fatty acid connected to the Lys26 via glutamyl. Liraglutide can bind non-covalently to albumin in plasma and retain the antagonism activity of GLP-1 against DPP IV degradation, and has a prolonged half-life of 11-15 hours that is suitable for administration once a day (Elbrond B, Diabetes Care, 2002, 25: 1398-1404). Another GLP-1 analogue, CJC-1131, can bind covalently to Cys34 of albumin in plasma after modification of Lys37 at the C-terminal in vitro, thus leading to administration once a day (Kim, J G, Diabetes, 2003, 52: 751-759). It follows that bioactivity can be well retained with substitution, deletion, and addition of (one or several) amino acids at the C-terminal of GLP-1 or exendin-4 by chemical or genetic engineering methods.

Many patent publications and literatures about GLP-1 and human FGF-21 (such as Christopher P. Prior, PCT/US03/26818; Craig A Rosen, US2006/0194735A1; Wolfgang Glaesner, US2007/0036806, PCT/US04/16611; Thomas P. CUJEC, US2008/0255045A1) show that, with fused expression of GLP-1 or FGF-21 together with human blood albumin, Fc fragment of human IgG or human transferrin, respectively, (GLP-1-HAS, GLP-1-Fc, GLP-1-Transferrin, FGF-21-HAS, FGF-21-Fc), the half-life of GLP-1 or FGF-21 in vivo can be prolonged to achieve injection once a week at most. Also, PEG-GLP-1 and PEG-FGF-21 which are chemically modified with PEG can achieve a better half-life in vivo.

In conclusion, GLP-1 and FGF-21 are polypeptide drugs against diabetes that are nowadays paid much attention; the former has clear structure and function as well as pharmaceuticals granted by FDA; and the latter was found for the first time in 2004 to be antidiabetic and hypolipemic in animal experiments. Clinically, hyperglycemia occurs often with hyperlipidemia, however, there are no drugs that can simultaneously regulate plasma glucose and lipid, and possess with longer half-lives.

DETAILS OF THE INVENTION

Based on forementioned techniques, the invention provides a fusion peptide of GLP-1 or its analogue Exendin-4 and human FGF-21, which simultaneously regulate plasma glucose and lipid and possesses with longer half-life. The fusion peptide can be used in preparation of drugs treating hyperglycemia- and hyperlipidemia-related diseases, such as diabetes, obesity, fatty liver, hyperlipidemia metabolism syndrome or cadiovascular diseases.

Provided is a fusion protein regulating plasma glucose and lipid, wherein the peptide chain is conjugated from N- to C-terminal as followings: R1-R2, R2-R1, R1-L-R2, and R2-L-R1; wherein, R1 is human fibroblast growth factor 21, or mutants or active fragments thereof; R2 is glucagon-like-peptide-1 or analogues thereof, or mutants or active fragments thereof; and L is a linker.

Preferably, said peptide chain is conjugated from N- to C-terminal as R2-R1 or R2-L-R1.

The amino acid sequence of said human fibroblast growth factor 21 is shown in SEQ ID NO: 1; and mutants or active fragments thereof are peptides comprising amino acid sequence with substitution, deletion or addition of one or several of amino acid residues of SEQ ID NO: 1, while remaining bioactivities and functions.

The amino acid sequence of said glucagon-like-peptide-1 is shown in SEQ ID NO: 2; and mutants or active fragments thereof are peptides comprising amino acid sequence with substitution, deletion or addition of one or several of amino acid residues of SEQ ID NO: 2, while remaining bioactivities and functions.

Said analogue of glucagon-like-peptide-1 is Exendin-4, which has amino acid sequence of SEQ ID NO: 3.

Said derivatives of analogue of glucagon-like-peptide-1 (Exendin-4) are peptides comprising amino acid sequence with substitution, deletion or addition of one or several of amino acid residues of SEQ ID NO: 3, while remaining the same bioactivities and functions as those comprising amino acid sequence of SEQ ID NO: 2.

Said linkers comprise 5-30 amino acids.

Said linkers are:

(a) $(Gly-Gly-Gly-Gly-Ser)_n-(Ser)_m$, wherein n is an integer between 1-5, and m is 0 or 1, their amino acid sequences as SEQ ID No. 17~26;

(b) $(Gly-Gly-Gly-Gly-Gly)_n-(Ser)_m$, wherein n is an integer between 1-5, and m is 0 or 1, their amino acid sequences as SEQ ID No. 27~36;

(c) $(Gly-Gly-Gly-Gly-Ser)_n-(Ser-Pro)_m$, wherein n is an integer between 1-5, and m is 0 or 1, their amino acid sequences as SEQ ID No. 17~21, 37~41;

(d) (Pro-Glu-Ala-Pro-Thr-Asp)$_n$, wherein n is an integer between 1-5, their amino acid sequences as SEQ ID No. 42~46; and/or (e) (Ser-Ser-Ser-Ser-Gly)$_n$-(Ser-Pro)$_m$, wherein n is an integer between 1-5, and m is 0 or 1, their amino acid sequences as SEQ ID No. 47~56.

Also provided is a gene fragment encoding the above fusion protein.

Also provided is a vector comprising the above gene fragment.

Also provided is a host cell containing the above vector.

Said host cell includes *E. coli*, yeast and CHO.

Also provided is a method for preparing the above fusion protein, comprising:

(a) cultivating said host cell to express said fusion protein; and (b) separating and purifying said fusion protein.

Also provided is use of the above fusion protein in preparing drugs treating diabetes, obesity, fatty liver and hyperlipidemia metabolism syndrome.

Also provided is a drug comprising any one of the above fusion protein.

In the first aspect of the invention, provided is a fusion protein that comprises amino acid sequences of human fibroblast growth factor 21 (FGF-21) and glucagon-like-peptide-1 (GLP-1 or Exendin-4), as well as a linker sequence of 5-30 amino acids between the two. The amino acid sequence of human fibroblast growth factor 21 (FGF-21) may be either located at the N-terminal, or the C-terminal of the fusion protein. Preferably, human FGF-21 is located at the C-terminal of the fusion protein. The fusion protein have combined bioactivities of GLP-1 and FGF-21, including: (1) inhibiting the synthesis of glucagon, thus reducing the release of glycogen at liver; (2) improving β-cell performance in pancreas islet and promoting the propagation; (3) enhancing the sensibility of insulin without risking of hypoglycemia or weight-gain, etc.; (4) facilitating fat metabolism. The blood sugar is regulated by the two via related receptors from different target cells, or via different receptors from the same target cells. FGF-21 lowers the blood sugar insulin-independently and regulates the fat metabolism in fat cells, thus reducing lipid. Meanwhile, blood sugar and lipid regulation of FGF-21 can be enhanced by GLP-1, which regulates the intestinal evacuation and lowers appetite.

Linkers connecting human FGF-21 and GLP-1, or exendin-4, comprise various sequences, such as (GGGGG)$_n$ (SEQ ID NO: 27), (GGGGS)$_n$ (SEQ ID NO: 17), (SGGGG)$_n$ (SEQ ID NO: 57), and (SSSSG)$_n$ (SEQ ID NO: 47), etc., wherein n is an integer from 1-5; thereby generating linkers of 5 to 30 amino acids. Sequences of serines or prolines may be added into linker sequences, which can also achieve the aim of the invention. Said linkers may be any combination of the above sequences.

Besides of natural human GLP-1 sequence (SEQ ID NO: 2), GLP-1 can also comprise mutants or derivatives thereof, or similar peptides sharing homology of more than 40% with SEQ ID NO: 2, while retaining biological function. Analogues of GLP-1 are mainly Exendin-4, which comprises amino acid sequence of SEQ ID NO: 3. Exendin-4 possesses of better specificity than natural GLP-1, as well as resistance to enzymatic degradations from DDP IV and other peptidases, and improved affinity to GLP-1 receptors.

In the second aspect of the invention, provided is a DNA molecule encoding the above fusion protein of the invention, as well as nucleotide sequence thereof, as shown in SEQ ID NO: 10.

In the third aspect of the invention, provided is an expression vector comprising any one of the above DNA molecule and preparation method thereof.

In the fourth aspect of the invention, provided is a host cell containing any one of the above expression vector.

In the fifth aspect of the invention, provided is a method for preparing the fusion protein of the present invention, including steps of: cultivating said host cell to express said fusion protein under conditions suitable for the expression; and separating and purifying said fusion protein.

The fusion protein of the invention allows simultaneous regulation of blood sugar and lipid from combined function of GLP-1, or exendin-4, and human FGF-21; as well as prolonged plasma half-lives. The main use thereof is for the active component of drugs treating metabolic disorders, such as hyperglycemia, hyperlipidemia, etc., with the addition of pharmaceutically acceptable vectors or excipients or diluents.

Definitions

As used herein, the term "fusion protein of FGF-21 and GLP-1" refers to proteins fused by amino acid sequences of human fibroblast growth factor 21 and glucagon-like-peptide-1 (GLP-1 or Exendin-4), wherein amino acid sequence of human fibroblast growth factor 21 may be located either at the N-terminal or the C-terminal of the fusion protein; with or without linker sequences between the two.

As used herein, the term "amino acid sequence of human fibroblast growth factor 21" in the fusion protein refers to one part of amino acid sequence in said fusion protein, which may be amino acid sequence of SEQ ID NO: 1 in the sequence list; or amino acid sequences derived from SEQ ID NO: 1 by substitution, deletion or addition of one or several of amino acid residues, while retaining the same activities.

As cited herein, the term "amino acid sequence of glucagon-like-peptide-1 (GLP-1 or Exendin-4)" in the fusion protein refers to one part of the amino acid sequence in said fusion protein, which may be amino acid sequence of SEQ ID NO: 2 or SEQ ID NO: 3 in the sequence list; or amino acid sequences derived from SEQ ID NO: 2 or SEQ ID NO: 3 by substitution, deletion or addition of one or several of amino acid residues, while retaining the same activities.

As cited herein, the term "linker" refers to a short peptide located between the amino acid sequences of human fibroblast growth factor 21 and glucagon-like-peptide-1 (GLP-1 or Exendin-4) that conjugates the two. The length of a linker is usually 5-30 amino acids. Linkers can be designed according to routine methods in the area. Usually, linkers do not affect or not severely affect the correct folding and conformation of amino acid sequences of fibroblast growth factor 21 and glucagon-like-peptide-1.

The cDNA sequence encoding the fusion protein of the present invention can be synthesized artificially, or by conjugating DNA sequences encoding FGF-21 and GLP-1, which are amplified by PCR or synthesized artificially.

The DNA sequence of the present fusion protein is inserted into a suitable expression vector, which is then transformed into a suitable host cell, followed by cultivation of the transformed cells and purification of the fusion protein of the invention.

As used herein, the term "vector" comprises plasmid, expression vector, cloning vector and virus vector.

As used herein, the term "host cell" comprises procaryotic and eucaryotic cell. Common procaryotic host cells include *E. coli* and *Bacillus subtilis*; and common eucaryotic host cells include yeast, CHO and HEK293 cells. The vector comprising the DNA sequence of target gene can be transformed into a host cell by methods known in the art, depending on the type of the host cell. For example, calcium chloride transformation method is usually used for procaryotic cells, while electroporation is often suitable for other host cells.

As used herein, the term "purification method" refers to routine purification methods known in the art, including ion-exchange column chromatography, hydrophobic interaction chromatography, reverse phase chromatography, dialysis, ultrafiltration, molecular exclusion chromatography; and a fusion protein with more than 95% purity is obtained, which is assayed by SDS-PAGE and RP-HPLC.

The invention is described in details hitherto, and can be further illustrated with reference to the following examples, which are not meant to limit the present invention.

DESCRIPTION OF DRAWINGS

FIG. 1: The amino acid sequence of human FGF-21 (SEQ ID NO: 1).
FIG. 2: Alignment of amino acid sequences of GLP-1 (7-37) (SEQ ID NO: 2) and Exendin-4 (SEQ ID NO: 3).
FIG. 5: The construction of pGAPZαA-Ex-4-$L_6$-F21.

EXAMPLES

Example 1

Recombinant Expression and Preparation of the Fusion Protein Met-Exendin-4-GGGGGS-FGF21 (D-Ex-4-$L_6$-F21) in *E. coli*

In this example, the involved fusion protein of GLP-1 and FGF-21 had a structure of Met-Exendin-4-GGGGGS-FGF21. The entire amino acid sequence of Exendin-4 and FGF-21 was synthesized according to the code preference of *E. coli* by TaKaRa Biotechnology (DaLian) co., ltd. cDNA sequence of FGf-21 set forth in SEQ ID NO: 4, and the cDNA sequence of Exendin-4 set forth in SEQ ID NO: 5.

4 primers were synthesized, namely P1, P2, P3, and P4.

```
                                        (SEQ ID NO: 6)
P1: 5'-GC CAT ATG CAT GGT GAA GGT ACC-3'

(SEQ ID NO: 7)
P2: 5'-GAGAACCACCGCCGCCACCAGATGGAGGTGGGGCACCAG-3'

(SEQ ID NO: 8)
P3: 5'-CTGGTGGCGGCGGTGGTTCTCACCCAATCCCAGATTCTA-3'

(SEQ ID NO: 9)
P4: 5'-GC GGA TCC TTA TCA TGA TGC ATAA-3'
```

Note that the GC in P1 was primer-protection bases and CATATG was restriction enzyme cutting site of NdeI; and the GC in P4 was primer-protection bases and GGATCC was restriction enzyme cutting site of BamHI.

Exendin-4 gene was amplified using Exendin-4 cDNA sequence as a template, and P1 and P2 as primers (with a NdeI restriction enzyme cutting site at the beginning of P1 and nucleotide sequence encoding the linker GGGGGS (SEQ ID NO: 32) at the end of P2); FGF-21 gene was amplified using FGF-21 DNA sequence as a template, and P3 and P4 as primers (with nucleotide sequence encoding the linker GGGGGS (SEQ ID NO: 32) at the beginning of P3 and a BamHI restriction enzyme cutting site and a terminator codon at the end of P4); and Met-Exendin-4-GGGGGS-FGF21 gene was amplified using the above fragments of Exendin-4 and FGF-21 as templates, and P1 and P4 as primers. The amplified M-Exendin-4-GGGGGS-FGF21 gene was thus added with NdeI and BamHI restriction enzyme cutting sites at the beginning and the end, respectively, to be inserted into a procaryotic expression vector pET-3C.

A PCR kit (TaKaRa, DaLian) was used for overlap extension PCR amplification of Met-Exendin-4-GGGGGS-FGF21 gene according to the instruction of manufacturer, under conditions of: 94° C. 1 min, 56° C. 1 min, and 72° C. 1 min for 30 cycles; with denaturation of 94° C., 10 min at the first cycle, and extension of 72° C. 10 min at the last. Results showed that target bands of 120 by (Exendin-4), 560 by (FGF-21), and 700 by (Met-Exendin-4-GGGGGS-FGF21, SEQ ID NO: 10) were obtained, respectively.

Figure 4:
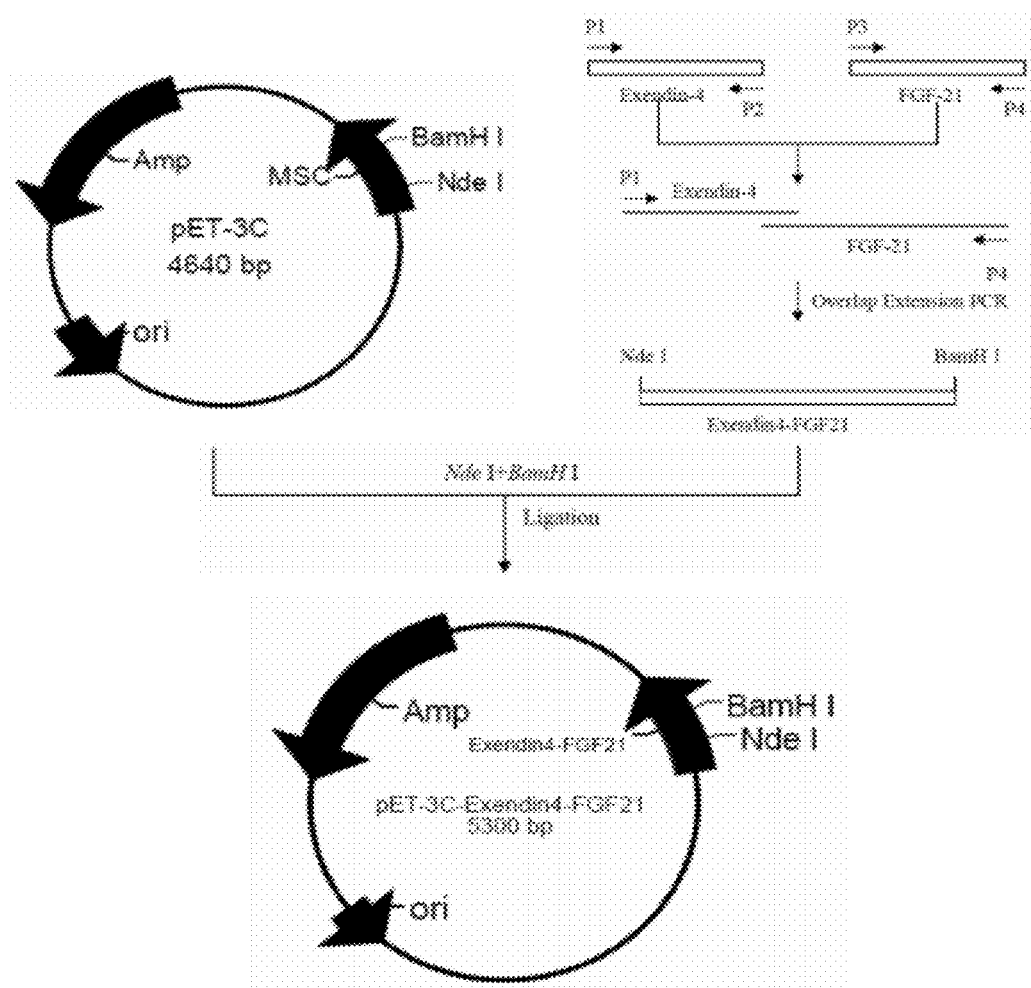
FIG. 4: The construction of pET-3C-Ex-4-$L_6$-F21.
Figure 3:
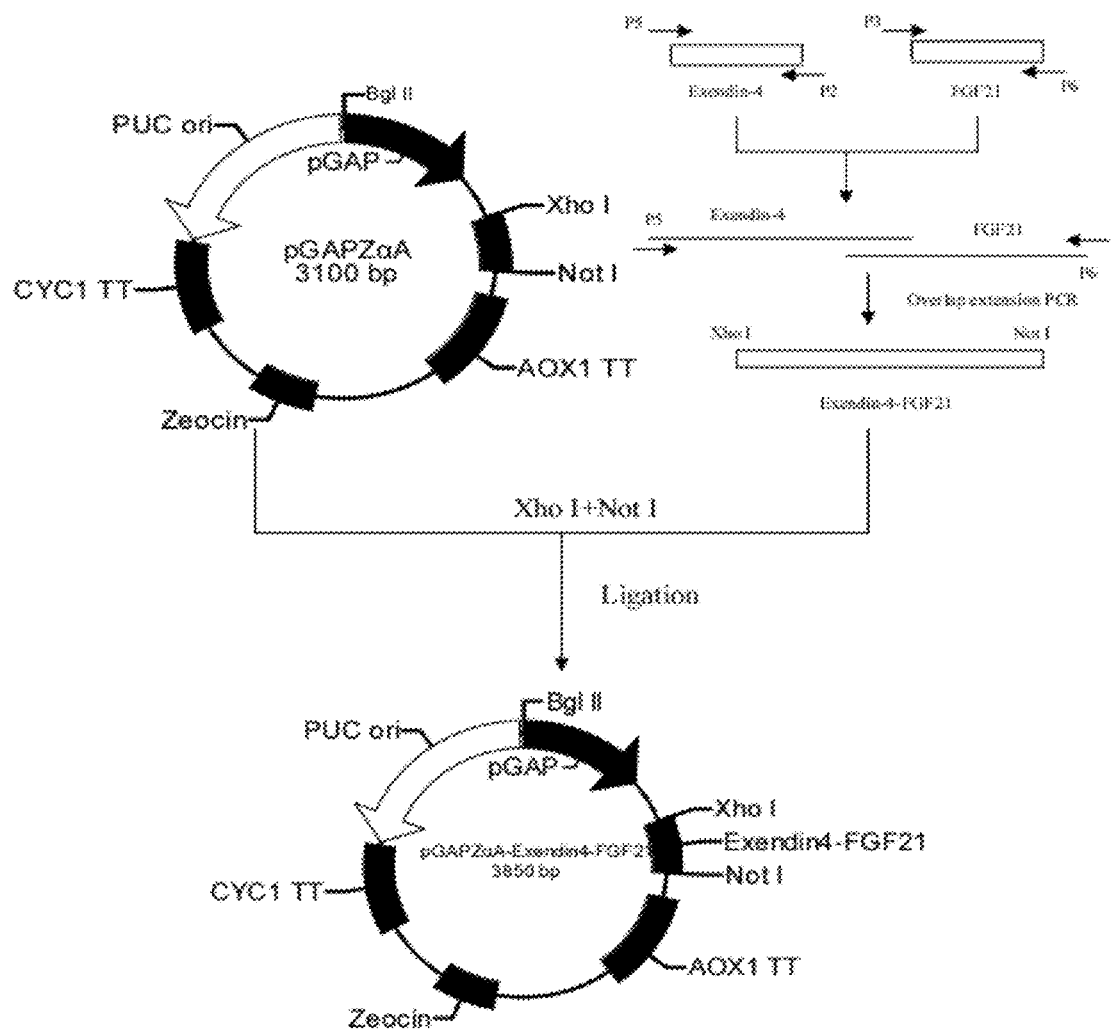
FIG. 3: The amino acid (SEQ ID NO: 58) and corresponding cDNA sequence (SEQ ID NO: 10) of fusion protein Exendin-4-GGGGGS-FGF21 (Ex-4-$L_6$-F21).

PCR product was purified by low melting agarose and digested with NdeI and BamHI; and the target fragment was recovered and linked by T4 DNA ligase into a plasmid pET-3C (from Invitrogen) that was also digested with NdeI and BamHI, to transform *E. coli* strain DH5α for cloning. Recombinant plasmid pET-3C-Exendin-4-GGGGGS-FGF21 was screened by enzymatic digestion and PCR amplification (FIG. 4), and the sequence was testified to be identical with the design (SEQ ID NO: 10) by DNA sequencing (TaKaRa, DaLian). The above plasmid was transformed into *E. coli* expression strain BL21 Star (DE3) plysS (Novagen), to construct the recombinant strain of pET-3C-Exendin-4-GGGGGS-FGF21/BL21 Star (DE3) plysS.

Figure 6:
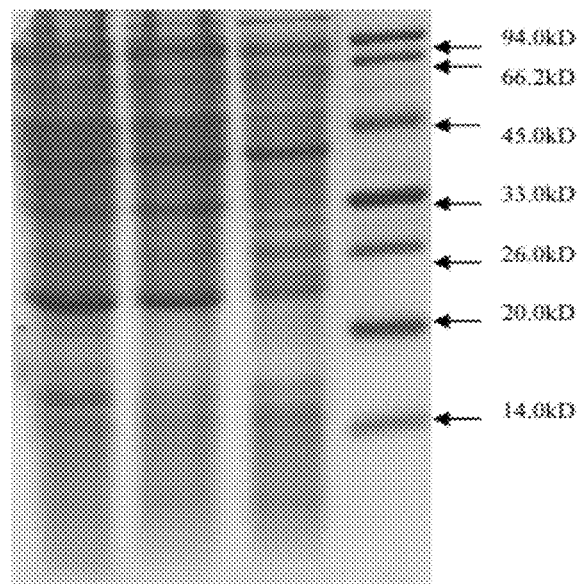
FIG. 6: SDS-PAGE of recombinant expression of pET-3C-Ex-4-$L_6$-F21 (from left: Band 1, 4 hours after induction; Band 2, 3 hours after induction; Band 3, control; and Band 4, the marker)

Recombinant strain with the best expression result was streak innoculated onto LA agar plate and cultured overnight at 37° C. Colony was picked up from the plate to innoculate LB liquid medium (comprising Tryptone 10 g, Yeast extract 5 g, NaCl 10 g, added with water to 1000 mL; sterilized for 30 min under 121° C. and high pressure) in a tube and cultured at 37° C. for 12 hours, followed by being innoculated by 1% into a 1000 mL flask containing 200 mL of LB, and cultured overnight at 37° C. to produce seed solution. The seed solution was then innoculated by 5% into a 30 L tank containing YT culture medium, and cultivated at 37° C. During the fermentation process, DO was maintained above 30% by regulating the agitation rate and the amount of air or oxygen, and pH was at 7.0 using 28% of ammonia water. 0.5 mmol/L of IPTG was added till $OD_{600}$=10-14, and the fermentation was terminated after 4 hours of continued cultivation (FIG. 6). The fermentation broth was collected by centrifugation at 8000 rpm for 10 min, wherein the supernatant was abandoned and the precipitate cells was preserved at −20° C.

Cells were added into lysis buffer (50 mmol/L Tris-HCl, 10 mmol/L EDTA, and 0.2 mg/mL lysozyme, pH 10) and stirred at 37° C. for 1 hour, then subjected to ultrasonic wave (400 W, 5 s for work and 5 s for interval, 40 cycles) and centrifugation at 12000 rpm for 10 min. The supernatant was abandoned and the precipitate was dissolved by Washing buffer A (20 mmol/L Tris-HCl, 10 mmol/L EDTA, 2 mol/L Urea, and 1% TritonX-100, pH 10), followed by stirring at 37° C. for 30 min, and centrifugation at 12000 rpm for 10 min. The supernatant was abandoned and the precipitate was washed by Solution B (20 mmol/L Tris-HCl, 4 mol/L Urea, 1.0 mol/L NaCl, pH 10), followed by stirring at 37° C. for 30 min and centrifugation at 12000 rpm for 10 min. The inclusion body (precipitate) was collected.

Dissolution and purification of the inclusion body: the inclusion body was dissolved by a solution (8 M urea, 5 mM ethanolamine, pH 11.5, 1/1000 β-ME, 2 mmol/L EDTA) and separated with Q-Sepharose FF after centrifugation. Q-Sepharose FF was balanced by a balance solution (8 M urea, 5 m Methanolamine, pH 11.5, 1/1000β-ME, 2 mmol/L EDTA) and loaded with samples, followed by re-balancing and linear elution with 0-500 mmol/L of NaCl. The elution peak containing the fusion protein was collected.

Renaturation: the fusion protein after Q-sepharose purification was placed in a Renaturation solution (20 mmol/L Tris-HCl, pH9.0) at 4° C. to be renatured by dialysis, or added into the Renaturation solution by 1:8 to be renatured for 12 hours.

Figure 7:
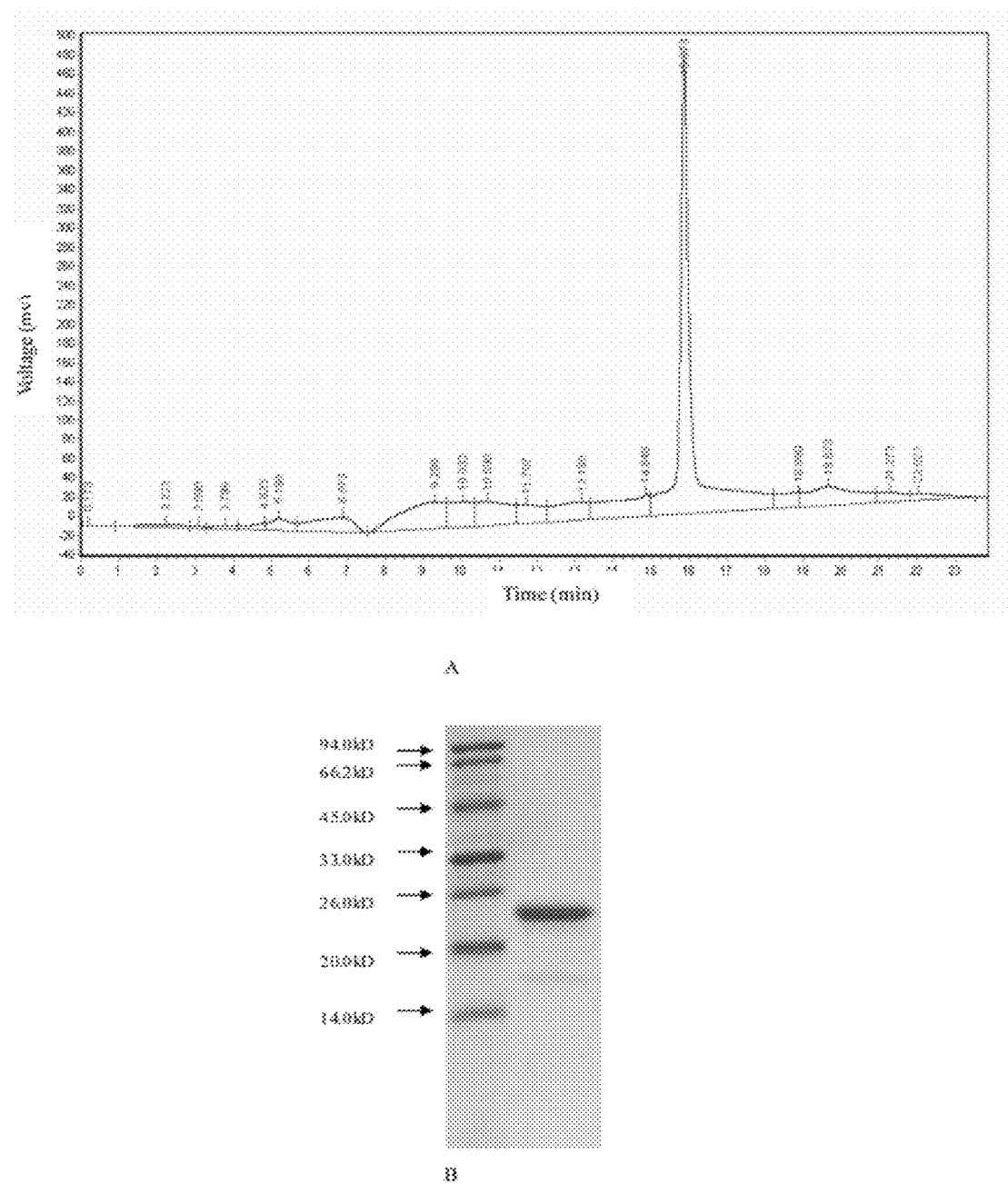
FIG. 7: RP-HPLC (a) and SDS-PAGE (b) (from left: Band 1, marker; Band 2, purified Exendin-4-FGF21) of purified Ex-4-$L_6$-F21.

Fine purification: the renatured solution was further purified by RP-HPLC (Waters Corp. $C_{18}$ column, with Mobile Phase Solution A (0.1% TFA, 5% acetonitrile), and Mobile Phase Solution B (0.1% TFA, 95% acetonitrile)) by linear elution with 0-100% of Solution B. Samples after RP-HPLC purification were then subjected to Superdex-75 (from Amersham Biosciences, buffered with PBS, pH 7.4) gel column, to obtain the recombinant fusion protein Met-Exendin-4-GGGGGS-FGF21 with purity of more than 95.0% (FIG. 7).

Example 2

Recombinant Expression and Preparation of Fusion Protein Met-Exendin-4-(GGGGS)$_3$-FGF21 (D-Ex-4-L$_{15}$-F21) in *E. coli*

In this example, the involved fusion protein of GLP-1 and FGF-21 had a structure of Met-Exendin-4-(GGGGS)$_3$-FGF21. The identified sequence of the recombinant plasmid pET-3C-Exendin-4-(GGGGS)-FGF21 in Example 1 was used as a template, and fusion protein comprising Met-Exendin-4-(GGGGS)$_3$-FGF21 was PCR amplified. Primers P1, P5, P6 and P4. were synthesized according to the design.

(SEQ ID NO: 6)
P1: 5'-GC CATATGCATGGTGAAGGTACC-3'

(SEQ ID NO: 11)
P5: 5'-GCC AGA GCC ACC GCC ACC GCT ACC GCC GCC ACC TGG AGG TG-3'

(SEQ ID NO: 12)
P6: 5'-AGC GGT GGC GGT GGC TCT GGC GGC GGT GGT TCT CAC CCA-3'

(SEQ ID NO: 9)
P4: 5'-GC GGA TCC TTA TCA TGA TGC ATA A-3'

Exendin-4 gene was amplified using P1 and P5 as primers [with a NdeI restriction enzyme cutting site at the beginning of P1 and nucleotide sequence encoding the linker (GGGGS)$_3$ (SEQ ID NO: 32) at the end of P5]; FGF-21 gene was amplified using P6 and P4 as primers (with nucleotide sequence encoding the linker (GGGGS)$_3$ (SEQ ID NO: 32) at the beginning of P3 and a BamHI restriction enzyme cutting site and a terminator codon at the end of P4); and Met-Exendin-4-(GGGGS)$_3$-FGF21 gene was amplified using the above fragments of Exendin-4 and FGF-21 as templates, and P1 and P4 as primers. The amplified M-Exendin-4-(GGGGS)$_3$-FGF21 gene was thus added with NdeI and BamHI restriction enzyme cutting sites at the beginning and the end, respectively, to be inserted into a procaryotic expression vector pET-3C.

Ex-4-L$_{15}$-F21 fusion protein was obtained with purity of more than 95.0% after the same steps of amplification, expression and purification as described in Example 1.

Example 3

Recombinant Expression and Preparation of Fusion Protein Met-Exendin-4-FGF21 (D-Ex-4-F21) in *E. coli*

In this example, the involved fusion protein of GLP-1 and FGF-21 had a structure of Met-Exendin-4-FGF21. Primers P1, P7, P8 and P4 were synthesized according to the design.

(SEQ ID NO: 6)
P1: 5'-GC CATATGCATGGTGAAGGTACC-3'

(SEQ ID NO: 13)
P7: 5'-AGA ATC TGG GAT TGG GTG TGG AGG TGG TGC ACC AGA-3'

(SEQ ID NO: 14)
P8: 5'-CAC CCA ATC CCA GAT TCT AGT CCA CTG TTA CAA TTC-3'

(SEQ ID NO: 9)
P4: 5'-GC GGA TCC TTA TCA TGA TGC ATA A-3'

Exendin-4 gene was amplified using Exendin-4 cDNA sequence as a template, and P1 and P7 as primers (with a NdeI restriction enzyme cutting site at the beginning of P1 and nucleotide sequence encoding FGF-21 at the end of P2); FGF-21 gene was amplified using FGF-21 DNA sequence as a template, and P8 and P4 as primers (with nucleotide sequence encoding Exendin-4 at the beginning of P3 and a BamHI restriction enzyme cutting site and a terminator codon at the end of P4); and Met-Exendin-4-FGF21 gene was amplified using the above fragments of Exendin-4 and FGF-21 as templates, and P1 and P4 as primers. The amplified M-Exendin-4-FGF21 gene was thus added with NdeI and BamHI restriction enzyme cutting sites at the beginning and the end, respectively, to be inserted into a procaryotic expression vector pET-3C.

Ex-4-F21 fusion protein was obtained with purity of more than 95.0% after the same steps of amplification, expression and purification as described in Example 1.

Example 4

Recombinant Expression and Preparation of Fusion Protein Met-Exendin-4-GGGGGS-FGF21 (G-Ex-4-L$_6$-F21) in Yeast In this example, the involved fusion protein of GLP-1 and FGF-21 had a structure of Exendin-4-GGGGGS-FGF21. Primers P9, P2, P3, and P10 were synthesized according to the design.

```
P9:  5' CTC GAG AAA AGA CAT GGT GAA GGT ACT TTT   (SEQ ID NO: 15)

ACC TCT GAT 3'

(SEQ ID NO: 7)
P2:  5' GAGAACCACCGCCGCCACCAGATGGAGGTGGGGCACCAG-3'

(SEQ ID -NO: 8)
P3:  5'CTGGTGGCGGCGGTGGTTCTCACCCAATCCCAGATTCTA3'

(SEQ ID NO: 16)
P10: 5'-GC GGCC GC TTA TCA TGA TGC ATA AGA AGG ACT

ACG ACC -3'
```

Exendin-4 gene was amplified using Exendin-4 cDNA sequence as a template, and P9 and P2 as primers (with a XhoI restriction enzyme cutting site at the beginning of P9 and nucleotide sequence encoding the linker GGGGGS (SEQ ID NO: 32) at the end of P2); FGF-21 gene was amplified using FGF-21 DNA sequence as a template, and P3 and P10 as primers (with nucleotide sequence encoding the linker GGGGGS (SEQ ID NO: 32) at the beginning of P3 and a NotI restriction enzyme cutting site and a terminator codon at the end of P10); and Exendin-4-GGGGGS-FGF21 gene was amplified using the above fragments of Exendin-4 and FGF-21 as templates, and P1 and P4 as primers. The fragment containing XhoI and NotI restriction enzyme cutting sites was then amplified and digested with XhoI and NotI, to be inserted into pGAPZαA and obtain the recombinant plasmid pGAPZαA-Exendin-4-GGGGGS-FGF21 (FIG. 5).

The recombinant plasmid pGAPZαA-Exendin-4-GGGGGS-FGF21 was linearized with AvrII and electrotransformed into *Pichia pastoris* GS115 (Invitrogen). Colonies with high copy were picked after His+ and Zeocin (1000 mg/ml) screen, inoculated into a 5 mL YPD medium, cultured overnight at 30°, and transferred into a 250 mL YPD medium and cultured for 96 hours. Supernatant was collected and ultrafiltrated before subjected to purification with Sepharose Q FF, $C_{18}$ column and Superdex-75, to prepare the recombinant fusion protein with purity of more than 95.0%.

Example 5

Recombinant Expression and Preparation of Fusion Protein Ex-4-(GGGGS)$_3$-F21 (G-Ex-4-L$_{15}$-F21) in Yeast In this example, the involved fusion protein of GLP-1 and FGF-21 had a structure of Exendin-4-(GGGGS)$_3$-FGF21. Primers P9, P5, P6, and P10 were synthesized according to the design.

```
                                                  (SEQ ID NO: 15)
P9:  5' CTC GAG AAA AGA CAT GGT GAA GGT ACT TTT

ACC TCT GAT 3'

(SEQ ID NO: 11)
P5:  5'-GCC AGA GCC ACC GCC ACC GCT ACC GCC GCC

ACC TGG AGG TG-3'

(SEQ ID NO: 12)
P6:  5'-AGC GGT GGC GGT GGC TCT GGC GGC GGT GGT

TCT CAC CCA-3'
```

```
                                                  (SEQ ID NO: 16)
P10: 5' GC GGCC GC TTA TCA TGA TGC ATA AGA AGG ACT

ACG ACC 3'
```

The fusion protein comprising the structure of Met-Exendin-4-(GGGGS)$_3$-FGF21 was amplified using the identified recombinant plasmid pET-3C-Exendin-4-(GGGGS) in Example 1 as a template. Exendin-4 gene was amplified using P9 and P5 as primers [with a XhoI restriction enzyme cutting site at the beginning of P9 and nucleotide sequence encoding the linker (GGGGS)$_3$ (SEQ ID NO: 32) at the end of P5]; FGF-21 gene was amplified using P6 and P10 as primers (with nucleotide sequence encoding the linker (GGGGS)$_3$ (SEQ ID NO: 32) at the beginning of P6 and a NotI restriction enzyme cutting site and a terminator codon at the end of P10); and Exendin-4-(GGGGGS)$_3$-FGF21 gene was amplified using the above fragments of Exendin-4 and FGF-21 as templates, and P9 and P10 as primers. The amplified M-Exendin-4-FGF21 gene was thus added with XhoI and NotI restriction enzyme cutting sites at the beginning and the end, respectively, to be inserted into the vector pGAPZαA.

The recombinant plasmid pGAPZαA-Exendin-4-FGF21 was linearized with AvrII and electrotransformed into *Pichia pastoris* GS115 (Invitrogen). Colonies with high copy were picked after His+ and Zeocin (1000 mg/ml) screen, innoculated into a 5 mL YPD medium, cultured overnight at 30°, and transferred into a 250 mL YPD medium and cultured for 96 hours. Supernatant was collected and ultrafiltrated before subjected to purification with Sepharose Q FF, $C_{18}$ column and Superdex-75, to prepare the recombinant fusion protein with purity of more than 95.0%.

Example 6

Recombinant Expression and Preparation of Fusion Protein Ex-4-F21 (G-Ex-4-F21) in Yeast In this example, the involved fusion protein of GLP-1 and FGF-21 had a structure of Exendin-4-FGF21. Primers P9, P7, P8, and P10 were synthesized according to the design.

```
                                                  (SEQ ID NO: 15)
P9:  5'-CTC GAG AAA AGA CAT GGT GAA GGT ACT TTT

ACC TCT GAT-3'

(SEQ ID NO: 13)
P7:  5'-AGA ATC TGG GAT TGG GTG TGG AGG TGG TGC

ACC AGA-3'

(SEQ ID NO: 14)
P8:  5'-CAC CCA ATC CCA GAT TCTAGT CCA CTG TTA CAA

TTC-3'

(SEQ ID NO: 16)
P10: 5'-GC GGCC GC TTA TCA TGA TGC ATA AGA AGG ACT

ACG ACC-3'
```

Exendin-4 gene was amplified using Exendin-4 cDNA sequence as a template, and P9 and P7 as primers (with a XhoI restriction enzyme cutting site at the beginning of P9 and nucleotide sequence encoding FGF-21 at the end of P2); FGF-21 gene was amplified using FGF-21 DNA sequence as a template, and P8 and P10 as primers (with nucleotide sequence encoding Exendin-4 at the beginning of P3 and a NotI restriction enzyme cutting site and a terminator codon at the end of P4); and Exendin-4-FGF21 gene was amplified using the above fragments of Exendin-4 and FGF-21 as templates, and P9 and P10 as primers. The amplified Exendin-4-FGF21 gene was thus added with XhoI and NotI restriction enzyme cutting sites at the beginning and the end, respectively, to be inserted into a eucaryotic expression vector pGAPZαA.

The recombinant plasmid pGAPZαA-Exendin-4-FGF21 was linearized with AvrII and electrotransformed into *Pichia pastoris* GS115 (Invitrogen). Colonies with high copy were picked after His+ and Zeocin (1000 mg/ml) screen, innoculated into a 5 mL YPD medium, cultured overnight at 30°, and transferred into a 250 mL YPD medium and cultured for 96 hours. Supernatant was collected and ultrafiltrated before subjected to purification with Sepharose Q FF, $C_{18}$ column and Superdex-75, to prepare the recombinant fusion protein with purity of more than 95.0%.

Example 7

GLP-1 Receptor Binding of Fusion Proteins Expressed in *E. coli* (Respectively, D-Ex-4-F21, D-Ex-4-$L_6$-F21 and D-Ex-4-$L_{15}$-F21) and Yeast (Respectively, G-Ex-4-F21, G-Ex-4-$L_6$-F21 and G-Ex-4-$L_{15}$-F21)

Figure 8:
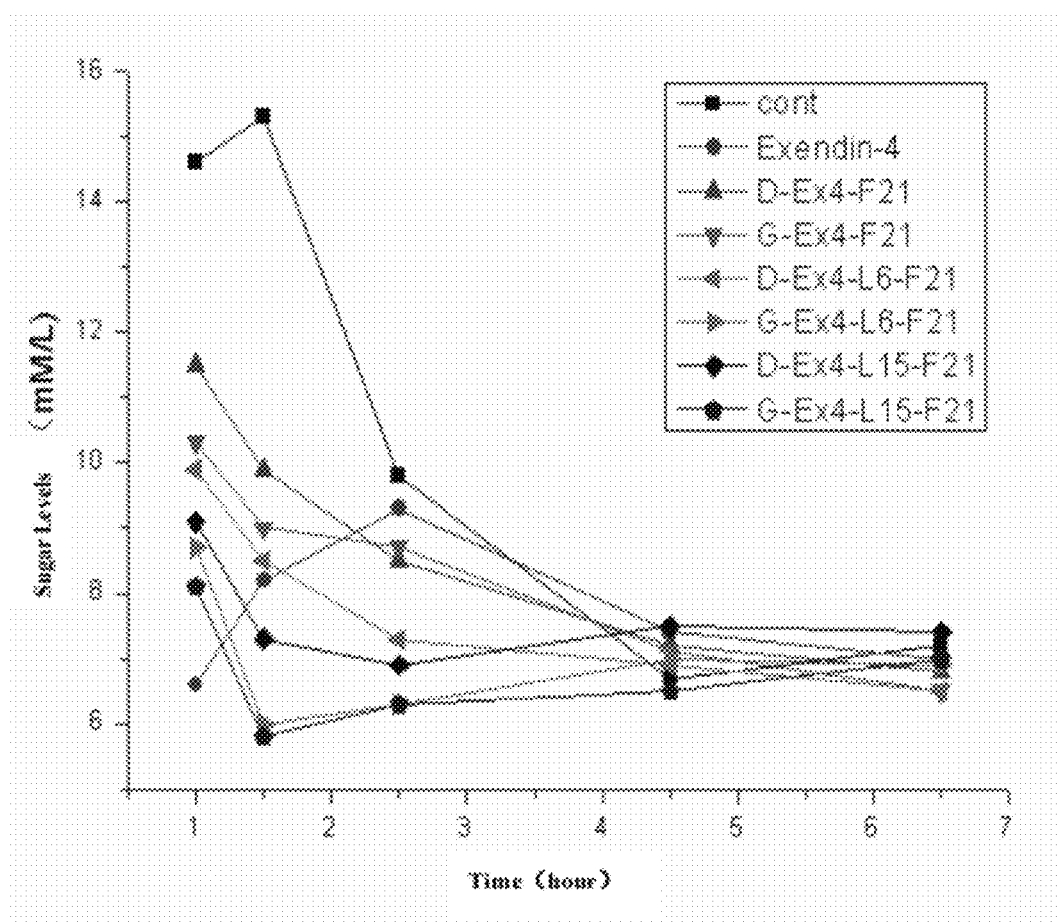
FIG. 8: Blood sugar regulation in vivo by D-Ex-4-F21, D-Ex-4-$L_6$-F21, D-Ex-4-$L_{15}$-F21, G-Ex-4-F21, G-Ex-4-$L_6$-F21 and G-Ex-4-$L_{15}$-F21 and Exendin-4 in mice.

Tolerance towards oral-taken glucose: Balb/c mice of 8-10 weeks (from Laboratory Animal Center, Chongqing Medical University, clean grade) were divided randomly into 8 groups, 15 mice for each group, comprising: the blank control; Exendin-4 (synthesized by Xunti biotechnology Corp., Chengdu, the same with followings) control; and fusion proteins D-Ex-4-F21, D-Ex-4-$L_6$-F21, D-Ex-4-$L_{15}$-F21, G-Ex-4-F21, G-Ex-4-$L_6$-F21, and G-Ex-4-$L_{15}$-F21. After fasting (fed with water only) for 16-18 hours the day before experiments, mice were intraperitoneally injected with 25 μg/kg of D-Ex-4-F21, D-Ex-4-$L_6$-F21, D-Ex-4-$L_{15}$-F21, G-Ex-4-F21, G-Ex-4-$L_6$-F21, G-Ex-4-$L_{15}$-F21 and 5 μg/kg of Exendin-4 (with the same molar concentration of 1 nM), respectively. Glucose of 1.5 mg/kg weight was filled into stomach after 0.5 hour of drug administration. Blood was sampled after 30 min, 1 h, 2 h, 4 h, and 6 h of glucose administration and blood sugar was assayed. Results showed that the blood sugar level was well regulated after the administration of Exendin-4 and fusion proteins. Fusion proteins with same structure and different expression system, namely yeast, showed remarkable sugar regulation when compared to those expressed in *E. coli*. G-Ex-4-$L_6$-F21 performed similarly as Exendin-4 in the sugar regulation, while G-Ex-4-F21 showed 60% of the G-Ex-4-$L_6$-F21 activity, and G-Ex-4-$L_{15}$-F21 was about 10% better than G-Ex-4-$L_6$-F21. G-Ex-4-$L_{15}$-F2 and G-Ex-4-$L_6$-F21 showed the longest sugar regulation in vivo, with remarkable regulation after 2 hours of administration (FIG. 8).

Producing cAMP by induction: INS-1 cells were cultivated in a 24-well plate by $5 \times 10^4$ cell per well. Firstly, cells were cultured in a serum-free SF-RPMI medium with 100 μm/L of IBMX for 5 h, then SF-RPMI medium containing different concentration of Exendin-4, D-Ex-4-F21, D-Ex-4-$L_6$-F21, D-Ex-4-$L_{15}$-F21, G-Ex-4-F21, G-Ex-4-$L_6$-F21 or G-Ex-4-$L_{15}$-F21 was added (3 wells for each concentration), followed by culturing for 10 min and adding 1 mL of frozen ethanol to end the reaction. After lyophilization, the supernatant of cell culture was re-dissolved by a sodium acetate buffer of ⅛ volume, and assayed with a cAMP EIA kit (R&D Corp.), in which the cAMP level of INS-1 cell treated by D-Ex-4-$L_6$-F21 under glucose-free condition was taken as a base line. Results showed that, with the existence of 5 mM glucose, cAMP levels in INS-1 cells treated by Exendin-4 or various fusion proteins were increased significantly. Fusion proteins with the same structure and different expression system, namely yeast, showed remarkable sugar regulation, when compared to those expressed in *E. coli*. The cAMP level in cells treated by G-Ex-4-$L_6$-F21 was similarly as those by Exendin-4 of the same molar concentration, while G-Ex-4-F21 showed 30% less, and G-Ex-4-$L_{15}$-F21 was better.

Example 8

FGF-21 Receptor Binding of Fusion Proteins Expressed in *E. coli* and Yeast

Cell culture and induction of differentiation: 3T3-L1 preadipocyte was cultivated under 37° C., 5% $CO_2$ in DMEM (high glucose) containing 10% of FBS for 2 days, followed by culturing in DMEM (high glucose) containing 0.5 mmol/L of IBMX, 1 μmol/L of dexamethasone, and 10 mg/L of human insulin for 48 hours, and then changed with DMEM (high glucose) containing 10 mg/L of human insulin for 48 hours. Approximately 90% of 3T3-L1 cells after 8-12 days of induction of differentiation showed fat cell phenotype, and were used in experiments as followings.

Assays on glucose transfer: 3T3-L1 fat cells in 24-well plate were simultaneously added with culture medium (DMEM (high glucose) with 0.2% BSA) containing recombinant human FGF-21 (from Chongqing Fagen Biomedical Inc., the same with followings), D-Ex-4-F21, D-Ex-4-$L_6$-F21, D-Ex-4-$L_{15}$-F21, G-Ex-4-F21, G-Ex-4-$L_6$-F21, or G-Ex-4-$L_{15}$-F21, respectively, until the final concentration came to 0, 0.03, 0.15, 0.8, 4, 20 and 100 nM (3 wells for each concentration), and cultured at 37° C. for 24 hours.

Assays on the glucose uptake: cells were washed twice with heated (37° C.) KRP buffer (consisting of: NaCl 131.2 mmol/L, KCl 4.7 mmol/L, $MgSO_4$ 1.2 mmol/L, $CaCl_2$ 2.5 mmol/L, and $NaH_2PO_4$ 2.5 mmol/L, pH 7.4), and incubated in KRP buffer containing 1% of BSA and 0.2 μci/well of 2-deoxygen-(14C)-glucose (100 μl) at 37° C. for 1 hr. The glucose uptake was terminated by the addition of 10 μmol/l of cytochalasin B. Another group added with 10 μmol/L of cytochalasin B was set for non-specific uptake of 2-deoxygen-(14C)-glucose (the control), and the glucose uptake of each group was obtained by the measured value minus the control.

TABLE 1

Glucose uptake CPM with different protein final concentration (nm)

| Groups | 0 nM | 0.03 nM | 0.15 nM | 0.8 nM | 4 nM | 20 nM | 100 nM |
|---|---|---|---|---|---|---|---|
| FGF-21 | 1875 ± 215 | 1801 ± 247 | 2107 ± 167 | 2203 ± 233 | 3300 ± 25☆ | 5132 ± 280▼ | 5325 ± 263▼ |
| D-Ex4-F21 | 1903 ± 222 | 1989 ± 249 | 2032 ± 198 | 2103 ± 218 | 2686 ± 247˙ | 3542 ± 218* | 3903 ± 229* |
| G-Ex4-F21 | 1945 ± 227 | 2199 ± 193 | 2188 ± 172 | 2206 ± 185 | 3108 ± 234 | 4006 ± 233* | 4319 ± 241* |
| D-Ex4-$L_6$-F21 | 2083 ± 204 | 1990 ± 188 | 2157 ± 183 | 2252 ± 170 | 3685 ± 266▼ | 4579 ± 257▼ | 4874 ± 273▼ |
| G-Ex4-$L_6$-F21 | 2028 ± 187 | 2087 ± 229 | 2274 ± 218 | 2411 ± 170 | 4193 ± 276▼ | 5237 ± 268▼ | 5239 ± 269▼ |
| D-Ex4-$L_{15}$-F21 | 1849 ± 173 | 1896 ± 202 | 2209 ± 198 | 2315 ± 207 | 3838 ± 252▼ | 4796 ± 246▼ | 4882 ± 256▼ |
| G-Ex4-$L_{15}$-F21 | 2126 ± 190 | 2031 ± 204 | 2244 ± 191 | 2396 ± 236 | 4332 ± 281▼ | 5390 ± 262▼ | 5506 ± 275▼ |

˙$P < 0.05$,
*$P < 0.01$, when compared to FGF-21;
☆$P < 0.05$,
▼$P < 0.01$, when compared to the concentration of 0.8 nM Results showed that, above the concentration of 0.8 nM, all of the various fusion proteins and the recombinant human FGF-21 could promote the glucose uptake in fat cell. Fusion proteins with the same structure and different expression system, namely yeast, showed remarkable activities when compared to those expressed in *E. coli*. G-Ex-4-$L_6$-F21 performed similarly as FGF-21, G-Ex-4-F21 inferiorer than G-Ex-4-$L_6$-F21, and G-Ex-4-$L_{15}$-F21 better than G-Ex-4-$L_6$-F21.

Example 9

Ob/Ob Mice Model Experiment

Male ob/ob mice were used as an obesity model to evaluate the regulation of blood sugar and triglyceride by recombinant human FGF-21, Exendin-4 and fusion proteins G-Ex-4-$L_6$-F21 and G-Ex-4-$L_{15}$-F21.

Ob/ob mice of 8 weeks (from Dashuo Laboratory Animal Center, Chengdu) were divided randomly into 5 groups, 16 mice for each group, comprising: the control, FGF-21, Exendin-4, G-Ex-4-$L_6$-F21 and G-Ex-4-$L_{15}$-F21. Continuously, the control group was hypodermically injected with normal saline for 7 days; the FGF-21 group by 5.0 µg/kg per day for 7 days; the Exendin-4 group by 1.0 µg/kg per day for 7 days; and G-Ex-4-$L_6$-F21 and G-Ex-4-$L_{15}$-F21 group by 5.0 µg/kg per day for 7 days. Blood was sampled from the tail 1 hour after drug administration, to assay the concentration of blood sugar or fat.

TABLE 2

The blood sugar after 7 days of continuous drug administration ($\bar{x} \pm S$, n = 8)

| | The blood sugar concentration of ob/ob mice after drug administration (mM/L) | | | | |
|---|---|---|---|---|---|
| Groups | 0 day | 2 days | 4 days | 6 days | 7 days |
| Control | 15.9 ± 2.1 | 15.6 ± 1.9 | 15.7 ± 2.5 | 16.1 ± 2.2 | 16.5 ± 1.9 |
| FGF-21 | 15.8 ± 2.0 | 15.1 ± 2.0 | 14.9 ± 1.7 | 14.0 ± 1.9☆ | 13.4 ± 1.4* |
| Exendin-4 | 16.2 ± 2.3 | 15.2 ± 2.0 | 13.7 ± 2.1☆ | 12.3 ± 1.5* | 12.1 ± 1.7* |
| G-Ex4-$L_6$-F21 | 16.5 ± 1.8 | 14.4 ± 1.3 | 10.8 ± 1.2* | 9.72 ± 1.3* | 9.0 ± 1.0* |
| G-Ex4-$L_{15}$-F21 | 16.0 ± 1.9 | 14.0 ± 1.8 | 10.1 ± 1.4* | 9.38 ± 1.1* | 9.1 ± 1.0* |

☆$P < 0.05$,
*$P < 0.01$ when compared to the control

TABLE 3

The blood fat after 7 days of continuous drug administration ($\bar{x} \pm S$, n = 8)

| Groups | The blood triglyceride concentration of ob/ob mice after drug administration (mg/dl) | |
| --- | --- | --- |
| | 4 days | 7 days |
| Control | 124 ± 13.1 | 132 ± 15.2 |
| FGF-21 | 93 ± 14.4* | 82 ± 11.3* |
| Exendin-4 | 136 ± 19.3 | 124 ± 17.8 |
| G-Ex4-$L_6$-F21 | 87 ± 15.5* | 65 ± 10.0* |
| G-Ex4-$L_{15}$-F21 | 78 ± 13.3* | 57 ± 9.6* |

*$P < 0.01$ when compared to the control

Results showed that G-Ex-4-$L_6$-F21 and G-Ex-4-$L_{15}$-F21 effectively reduced the level of blood sugar and fat in ob/ob mice after 7 days of continuous drug administration.

Example 10

Effect of Fusion Proteins (G-Ex-4-$L_6$-F21 and G-Ex-4-$L_{15}$-F21) on the Fatty Liver in C57BL/6J Mice that was Caused by High Fat Diets C57BL/6J mice used in the experiment weighted for about 20 g and were fed with rodent feed of 60% fat energy from Research Diets Corp. (Item No: D12492), which comprises: casein, 200 g; cystine, 3 g; malt dextrin, 125 g; sucrose, 68.8 g; cellulose, 50 g; soybean oil, 25 g; lard, 245 g; complex minerals, 10 g; calcium hydrophosphate, 13 g; calcium carbonate, 5.5 g; potassium citrate, 16.5 g; complex vitamins, 10 g; and choline bitartrate, 2 g. After being fed continuously for 8 weeks, mice that weighted 20% more than normal ones were taken as models, and were divided randomly into 5 groups, 10 mice for each group, comprising: the control, FGF-21, Exendin-4, G-Ex-4-$L_6$-F21 and G-Ex-4-$L_{15}$-F21, together with the normal C57BL/6J mice as blank control. The model control and blank control groups were injected hypodermically with normal saline; the FGF-21 group by 5.0 μg/kg per day; the Exendin-4 group by 1.0 μg/kg per day; and G-Ex-4-$L_6$-F21 and G-Ex-4-$L_{15}$-F21 groups by 5.0 μg/kg per day; each with continuous administration for 30 days, during which high fat diets and normal water were supplied. Blood was sampled at 1 hour after the last drug administration to assay triglyceride (TG), total cholesterol (TC), low-density lipoprotein (LDL), and high-density lipoprotein (HDL). Livers were taken for pathological examination.

The liver pathological examination showed that, the normal mice had regular hepatic lobules radiating around the central vein, normal arrangement of hepatic cords, circular and regular karyons and no lipid droplet piled in liver cells. The control and Exendin-4 groups had unclear hepatic lobules, partial loss of hepatic cords, disorders in the liver cell arrangement, diffused fatty degeneration in liver cells, as well as focal necrosis, more chronic inflammatory cell infiltration and a few neutrophilic granulocyte infiltration. While G-Ex-4-L6-F21, G-Ex-4-L15-F21 and FGF21 groups had alleviated fatty liver degeneration, survived hepatic lobules, roughly normal liver tissues, partial disorders in hepatic cord arrangement, narrowed hepatic sinusoids, and mild oedema and fatty degeneration of liver cells around headers.

TABLE 4

The blood fat after 30 days of continuous drug administration ($\bar{x} \pm S$, n = 10)

| Groups | TG (mmol/l) | TC (mmol/l) | LDL (mmol/l) | HDL (mmol/l) |
| --- | --- | --- | --- | --- |
| Blank control | 0.63 ± 0.15* | 1.36 ± 0.28* | 0.30 ± 0.11* | 1.12 ± 0.36* |
| Control | 9.38 ± 2.24 | 3.11 ± 1.03 | 2.45 ± 0.61 | 0.56 ± 0.18 |
| FGF-21 | 3.53 ± 1.21* | 1.95 ± 0.62☆ | 1.26 ± 0.38☆ | 0.92 ± 0.20☆ |
| Exendin-4 | 9.03 ± 2.45 | 3.31 ± 1.25 | 2.18 ± 0.78 | 0.43 ± 0.11 |
| G-Ex4-$L_6$-F21 | 2.95 ± 0.83* | 2.12 ± 0.77☆ | 0.97 ± 0.25* | 1.23 ± 0.40* |
| G-Ex4-$L_{15}$-F21 | 2.65 ± 0.78* | 1.76 ± 0.68* | 0.90 ± 0.28* | 1.28 ± 0.39* |

☆$P < 0.05$,

*$P < 0.01$ when compared to the control

Results showed that, after 30 days of continuous drug administration, G-Ex-4-L$_6$-F21, G-Ex-4-L$_{15}$-F21 and FGF-21 effectively reduced triglyceride, total cholesterol and low-density lipoprotein in model animals; and elevated high-density lipoprotein level, thus contributed a lot to the treatment of fatty livers, whereas Exendin-4 exhibited no significant effects on fat metabolism.

The invention claimed is:

1. A fusion protein having a formula of R2-R1 or R2-L-R1, wherein:
   R1 is a human fibroblast growth factor 21;
   R2 is Exendin-4; and
   L is a linker.

2. The fusion protein according to claim 1, wherein the Exendin-4 has the amino acid sequence of SEQ ID NO: 3.

3. The fusion protein according to claim 1, wherein the linker is:
   (a) (Gly-Gly-Gly-Gly-Ser)$_n$-(Ser)$_m$, wherein n is an integer between 1-5, and m is 0 or 1;
   (b) (Gly-Gly-Gly-Gly-Gly)$_n$-(Ser)$_m$, wherein n is an integer between 1-5, and m is 0 or 1;
   (c) (Gly-Gly-Gly-Gly-Ser)$_n$-(Ser-Pro)$_m$, wherein n is an integer between 1-5, and m is 0 or 1;
   (d) (Pro-Glu-Ala-Pro-Thr-Asp)$_n$, wherein n is an integer between 1-5; or
   (e) (Ser-Ser-Ser-Ser-Gly)$_n$-(Ser-Pro)$_m$, wherein n is an integer between 1-5, and m is 0 or 1.

4. The fusion protein according to claim 1, wherein the human fibroblast growth factor 21 comprises the amino acid sequence of SEQ ID NO: 1.

5. A polynucleotide, which encodes a fusion protein, wherein the fusion protein has a formula of R2-R1 or R2-L-R1, wherein:
   R1 is a human fibroblast growth factor 21;
   R2 is Exendin-4; and
   L is a linker.

6. A vector, which comprises a polynucleotide, wherein the polynucleotide encodes a fusion protein, and wherein the fusion protein has a formula of R2-R1 or R2-L-R1, wherein:
   R1 is a human fibroblast growth factor 21;
   R2 is Exendin-4; and
   L is a linker.

7. A host cell, which contains a vector, wherein the vector comprises a polynucleotide, wherein the polynucleotide encodes a fusion protein, wherein the fusion protein has a formula of R2-R1 or R2-L-R1, wherein:

R1 is a human fibroblast growth factor 21;
R2 is Exendin-4; and
L is a linker.

8. The host cell according to claim 7, which is selected from *E. coli*, yeast and CHO.

9. A method for preparing a fusion protein, comprising steps of:
   (a) cultivating a host cell selected from *E. coli*, yeast and CHO to express said fusion protein, wherein the host cell contains a vector having a polynucleotide encoding the fusion protein, wherein the fusion protein has a formula of R2-R1 or R2-L-R1, wherein:
   R1 is a human fibroblast growth factor 21;
   R2 is Exendin-4; and
   L is a linker; and
   (b) separating and purifying said fusion protein.

10. A fusion protein having a formula of R2-R1 or R2-L-R1, wherein:
    R1 is a mutant of human fibroblast growth factor 21 comprising the amino acid sequence of SEQ ID NO: 1 having up to four N-terminal amino acids deleted from the amino acid sequence of SEQ ID NO: 1, and has the bioactivity and function of FGF-21 comprising the amino acid sequence of SEQ ID NO: 1;
    R2 is Exendin-4; and
    L is a linker.

* * * * *